United States Patent [19]

Shanklin, Jr.

[11] Patent Number: 4,895,840
[45] Date of Patent: Jan. 23, 1990

[54] N-(ARYL-,ARYLOXY-,ARYLTHIO-ARYL-SULFINYL-AND ARYLSULFONYL-)ALKYL-N,N'-(OR N'N')ALKYLAMINOALKYL UREAS AND CYANOGUANIDINES

[75] Inventor: James R. Shanklin, Jr., Richmond, Va.

[73] Assignee: A. H. Robins Company, Incorporated, Richmond, Va.

[21] Appl. No.: 60,266

[22] Filed: Jun. 10, 1987

[51] Int. Cl.$^4$ .................. C07C 127/17; C07C 157/07; A61K 31/17

[52] U.S. Cl. .................... 514/212; 514/331; 514/428; 514/583; 514/595; 514/212; 514/331; 514/428; 514/231.8; 514/232.2; 514/237.2; 540/596; 540/597; 540/610; 544/124; 544/152; 544/159; 544/160; 544/168; 544/360; 544/379; 544/398; 544/400; 546/193; 546/214; 546/246; 546/247; 546/291; 548/517; 548/561; 549/496

[58] Field of Search .................. 564/27, 49, 52; 540/596, 597, 610; 544/124, 152, 159, 160, 168, 360, 379, 398, 400; 546/193, 214, 246, 247, 291; 548/517, 561; 549/496; 514/212, 228, 232, 235, 237, 331, 428, 583, 545

[56] References Cited

U.S. PATENT DOCUMENTS

| | | | |
|---|---|---|---|
| 4,558,155 | 10/1985 | Shanklin | 564/27 |
| 4,563,469 | 1/1986 | Butler | 514/339 |
| 4,597,902 | 7/1986 | Shanklin | 564/27 |

Primary Examiner—Robert Gerstl

[57] ABSTRACT

Novel N-(Aryl-,aryloxy-,arylthio-,arylsulfinyl-and arylsulfonyl-)alkyl-N,N'-(or N',N')alkylaminoalkyl ureas, thioureas and cyanoguanidines represented by the following formula:

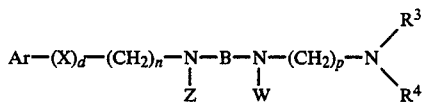

wherein Ar is aryl selected from the group consisting of 1- and 2-naphthyl, 2,3-dihydro-1H-inden-4(or 5)-yl,2-furanylmethyl,2-pyridinyl, phenyl and phenyl substituted by 1-3 radicals commonly used in the pharmaceutical art; $(X)_d$ is oxygen, thio, sulfinyl, sulfonyl or d is zero; Z and W are each R or-$(CH_2)_m$-$NR^1R^2$ wtih the proviso that when Z is R, W is-$(CH_2)_m$-$NR^1R^2$ and when Z is-$(CH_2)_m$-$NR^1R^2$, W is R; B is carbonyl, thioxomethyl, or cyanoiminomethyl; R, $R^1$, $R^2$, $R^3$ and $R^4$ are selected from the group consisting of hydrogen, loweralkyl, cycloalkyl, phenyl or phenyl-loweralkyl wherein phenyl may be substituted by 1-3 radicals commonly used in the pharmaceutical art; $R^1$ and $R^2$, and $R^3$ and $R^4$ may together with the adjacent nitrogen form the heterocyclic ring structure 1-homopiperidinyl, 4-morpholinyl, 1-piperazinyl, 4-substituted-1-piperazinyl, 1-pyrrolidinyl or 1-piperidinyl and the pharmaceutically acceptable salts thereof are disclosed. A pharmaceutical method for administering the compounds for their cardiac antiarrhythmic effect and pharmaceutical compositions for the treatment of cardiac arrhythmia are also disclosed.

63 Claims, No Drawings

N-(ARYL-,ARYLOXY-,ARYLTHIO-ARYLSULFI-NYL-AND ARYLSULFONYL-)ALKYL-N,N'-(OR N'N')ALKYLAMINOALKYL UREAS AND CYANOGUANIDINES

BACKGROUND OF THE INVENTION (1) Field of Invention

The present invention related to certain novel N-(aryl-, aryloxy-, arylthio-, arylsulfinyl- and arylsulfonyl-)alkyl-N,N'-(or N',N')alkylaminoalkyl ureas, thioureas and cyanoguanidines and the pharmaceutically acceptable acid addition salts and hydrate thereof, and pharmaceutical processes and compositions for administering the same to a living animal body for its cardiac antiarrhythmic effect.

(2) Information Disclosure Statement

Procainamide hydrochloride (4-amino-N-[2-(diethylamino)ethyl]benzamide monohydrochloride), has been used in the art to suppress certain cardiac arrhythmias.

Recently, Protiva, M. et al. have disclosed in Czeck Patent 146,873 [C.A. 79, 42205g] compounds such as m-ClC$_6$H$_4$O(CH$_2$)$_3$CONH(CH$_2$)$_2$N(C$_2$H$_5$)$_2$ useful for lowering blood sugar levels in rats.

Joullié M. et al., in U.S. Pat. No. 4,252,804 have disclosed 3,4,5-trimethoxybenzene derivatives which have the general structure (CH$_3$O)$_3$—C$_6$H$_2$—X—(CH$_2$)$_m$—Y—(CH$_2$)$_m$—NR$_1$R$_2$ wherein; X is oxygen or

(wherein R$_3$ represents a hydrogen atom, benzyl or mopholinoethyl group); Y represents one of the divalent groups Co, CONH, COO or SO$_2$ and NR$_1$R$_2$ can be selected from a list of possible values among which are dimethylaminopropylamino or N-methyl-N-dimethylaminopropylamino. These compounds are disclosed to be useful as myorelaxants, anticonvulsants and tranquilizers.

Koelzer, P. P. and Wehr, K. H. in Arzneim. Forsch 9, 113–120 (1959) disclosed two unsubstituted phenoxy urea compounds; namely, N'-[2-(diethylamino)ethyl]-N-methyl-N-[2-(phenoxy)ethyl]urea and N-methyl-N-[2-(phenoxy)ethyl]-N'-[2-(pyrrolidinyl)ethyl]urea. Anesthetic activity in animals was disclosed but clinical use of these ureas was said to be unlikely. There is no disclosure of thiourea compounds.

Certain N-(aryloxyalkyl)-N'-(aminoalkyl)ureas and thioureas are disclosed in U.S. Pat. Nos. 4,500,529 and 4,558,155 to have antiarrhythmic properties and have the general formula:

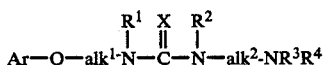

Wherein;

R$^1$ and R$^2$ are selected from the group consisting of hydrogen, loweralkyl, cycloalkyl, phenyl, phenyl substituted by halogen, loweralkyl or loweralkoxy or phenylloweralkyl and loweralkoxy, R$^3$ and R$^4$ are selected from the groups consisting of hydrogen, loweralkyl, loweralkoxy and phenylloweralkyl wherein phenyl may be substituted by halogen, loweralkyl, loweralkoxy, and R$^3$ and R$^4$ may be taken together with the adjacent nitrogen to form a heterocyclic residue, X is selected from oxygen or sulfur, Ar is selected from 1 and 2 naphthyl, 2,3-dihydro-1H-inden-4(or 5)-yl, 3-pyridinyl, phenyl or substituted phenyl, and alk$^1$ and alk$^2$ are selected from the group consisting of loweralkylene or loweralkylene-loweralkyl.

Certain N-(arylthioalkyl)-N'-(aminoalkyl)ureas and thioureas are diclosed in U.S. Pat. No. 4,597,902 to have a high degree of cardiac activity in animals which compounds have the structure:

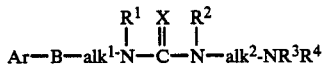

wherein B is thio, sulfinyl or sulonyl; R$^1$ and R$^2$ are hydrogen, loweralkyl, cycloalkyl, 2-furanyl, phenyl, phenylloweralkyl and substituted phenyl; R$^3$ and R$^4$ are hydrogen, loweralkyl, phenyl, phenylloweralkyl and substituted phenyl or R$^3$ and R$^4$ with adjacent nitrogen form a heterocyclic residue.

OBJECTS AND SUMMARY OF THE INVENTORY

The present invention is concerned with novel N-(Aryl-, arylthio-, arylsulfinyl- and arylsulfonyl-)alkyl-N,N'-(or N',N')alkylaminoalkyl ureas, thioureas and cyanoguanidines and utilization thereof for treating cardiac arrhythmias in a mammal in need thereof. The compounds have the structure:

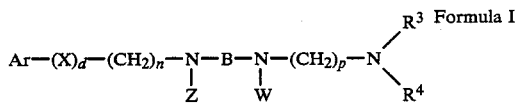

Formula I wherein Ar is 1- or 2-naphthyl, 2,3-dihydro-1H-inden-4(or 5)-yl, 2-furanylmethyl, 2-pyridinyl, phenyl or phenyl substituted by one to three radicals, the same or different, said radicals being selected from the group consisting of loweralkyl, loweralkoxy, diloweralkylamino, cyano, loweralkylthio, loweralkylsulfinyl, loweralkylsulfonyl, acyl, acylamino, aminocarbonyl, diloweralkylaminoloweralkoxy, trifluoromethyl, nitro and halogen;

X is thio, sulfinyl, sulfonyl, or oxygen;

d is zero or one;

B is carbonyl, thioxomethyl or cyanoiminomethyl;

n, m and p are selected from 2–6 inclusive and may be the same or different;

Z and W are each R or

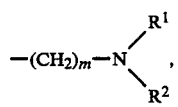

with the proviso that when Z is R, W is —(CH$_2$)$_m$—NR$^1$R$^2$ and when Z is —(CH$_2$)$_m$—NR$^1$R$^2$, W is R;

R, R$^1$, R$^2$, R$^3$ and R$^4$ may be the same or different and are selected from the group consisting of hydrogen, loweralkyl, cycloalkyl, phenyl and phenyl-loweralkyl, wherein phenyl may be substituted by one to three radicals, the same or different, said radicals being selected from the group consisting of loweralkyl, loweralkoxy, cyano, trifluoromethyl, nitro and halogen;

each of $R^1$ and $R^2$, and $R^3$ and $R^4$ may, together with the adjacent nitrogen form the heterocyclic ring structure 1-homopiperidinyl, 1-piperidinyl, 4-morpholinyl, 1-pyrrolidinyl, 1-piperazinyl, or 4-substituted-1-piperazinyl, with the further proviso that when B is thioxomethyl, then $R^1$, $R^2$, $R^3$ and $R^4$ are not hydrogen or with the adjacent nitrogen form the heterocyclic ring structure 1-piperazinyl; and with a still further proviso that when B is carbonyl and $(X)_d$ is thio or sulfinyl or Ar is phenyl substituted by loweralkylthio or loweralkylsulfinyl, then $R^1$, $R^2$, $R^3$ and $R^4$ are not hydrogen or with the adjacent nitrogen form the heterocyclic ring structure 1-piperazinyl; and with a still still further proviso that when B is cyanoiminomethyl and Z is $-(CH_2)m-NR^1R^2$ and $(X)_d$ is thio or sulfinyl or Ar is phenyl substituted by loweralkylthio or loweralkylsulfinyl, then $R^1$ and $R^2$ are not hydrogen or with the adjacent nitrogen form the heterocyclic ring structure 1-piperazinyl; and with a final proviso that when B is cyanoiminomethyl and W is $-(CH_2)m-NR^1R^2$ and $(X)_d$ is thio or sulfinyl or Ar is phenyl substituted by loweralkylthio or loweralkylsulfinyl then $R^1$, $R^2$, $R^3$ and $R^4$ are not hydrogen or with the adjacent nitrogen form the heterocyclic ring structure 1-piperazinyl;

and the pharmaceutically acceptable salts thereof.

In further definition of the symbols in the formulas hereof and where they appear elsewhere throughout this specification and the claims the terms have the following significance:

The term "loweralkyl" as used herein inludes straight and branched chained radicals of up to 8 carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula —O-loweralkyl.

The term "carbonyl" as used herein has the formula:

The term "thioxomethyl" as used herein hs the formula:

The term "cyanoiminomethyl" as used herein has the formula:

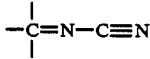

The term "halogen", "halo" or "halide" as used herein includes fluorine, chlorine, bromine and iodine, preferably fluorine, chlorine and bromine.

The term "heterocyclic ring structure" as used herein includes 1-pyrrolidinyl, 1-piperidinyl, 4-morpholinyl, 1-piperazinyl, 4-substituted-1-piperazinyl, and 1-homopiperidinyl.

The term "4-substituted-1-piperazinyl" of Formula I under the definition of heterocyclic residue refers to piperazine substituted in the 4-position by radicals common in the pharmaceutical art including loweralkyl, phenyl and phenyl substituted by 1-2 radicals such as halo, loweralkyl, loweralkoxy, trifluoromethyl, nitro, cyano and the like and pyridyl.

Protecting radicals such as phenylmethyloxycarbonyl, $\beta,\beta,\beta$-trichloroethoxycarbonyl, butoxycarbonyl and the like may be used in the preparation of unsubstituted piperazino compounds. See I. F. W. McOmie in the textbook "Protective Groups in Organic Chemistry" publ. by the Plenum Press, 1973, Chapter 2, pp. 43-93, for use of amine protecting radicals and deprotection thereof. Generally in the methods of preparations, the 4-piperazine, nitrogen should be protected during synthesis. If the piperazine has a substituent in the 4-piperazine nitrogen you would not have to protect, e.g., phenyl etc.

"Pharmaceutially acceptable salts" include acid addition salts, hydrates, alcoholates and quarternary salts of the compounds of Formula I, which are physiologically compatible in mammals. The acid addition salts may be formed by either strong or weak acids. Representative of strong acids are hydrochloric, sulfuric and phosphoric acids. Representative of weak acids are fumaric, maleic, succinic, oxalic, citric, tartaric, hexamic, and the like. Suitable quarternary salts include the loweralkyl halides and loweralkyl sulfates.

By "free base" is meant a compound in its non-salt form.

The term "cycloalkyl" as used herein includes primarily cyclic alkyl radicals containing 3 to 9 carbon atoms inclusive and includes such groups as cyclopropyl, cyclobutyl, cyclopentyl, cyclohexyl, methylcyclohexyl, cycloheptyl and the like.

The term "substituted phenyl" as used herein refers primarily to phenyl substituted by one to three radicals which may be the same or different and are selected from the group consisting of loweralkyl, loweralkoxy, cyano, trifluoromethyl, nitro and halogen.

The compounds of the present invention exhibit antiarrhythmic activity in dogs when arrhythmia is induced by a method of coronary artery ligation, the method is described more fully hereinbelow under pharmacology.

It is therefore an object of the present invention to provide certain novel N-(aryl-, aryloxy-, arylthio-, arylsulfinyl- and arylsulfonyl-)alkyl-N,N'-(or N',N')alkylaminoalkyl ureas, thioureas and cyanoguanidines and salts and hydrates thereof.

Another object of the invention is to provide methods and compositions for treating cardiac arrhythmias in living animal bodies utilizing certain N-(aryl-, aryloxy-, arylthio-, arylsulfinyl-, and arylsulfonyl-)alkyl-N',N-(or N',N')alkylaminoalkyl ureas, thiouras or cyanoguanidines.

Additional objects will become apparent to one skilled in the art and still other objects will become apparent hereinafter.

DETAILED DESCRIPTION OF THE INVENTION

The method of treating arrhythmias in living animals, comprises administring N-(aryl-, aryloxy-, arylthio-, arylsulfinyl-, and arylsulfonyl-) alkyl-N,N'-(or N',N')alkylaminoalkyl ureas, thioureas and cyanoguanidines and derivatives as set forth hereinabove under Formula I and as pharmaceutical compositions to a living animal body for cardiac arrhythmic effect in an amount effective to control arrhythmia. The compounds of Formula I wherein B is carbonyl or thioxomethyl are prepared by one of the four methods A, B, C, and D. Compounds wherein B is cyanoiminomethyl are prepared by one of the two methods E and F.

Method A—This method is represented by the following equations:

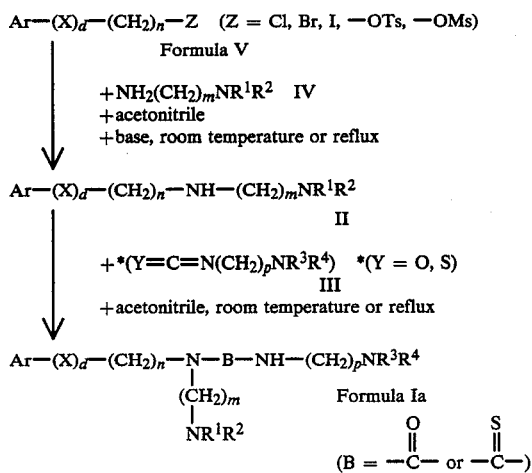

wherein;

Ar, X, d, n, m and p are as defined hereinabove under Formula I, and B is carbonyl or thioxomethyl and never cyanoiminomethyl in this method, and $R^1$, $R^2$, $R^3$ and $R^4$ are selected from loweralkyl, cycloalkyl, phenyl, phenylloweralkyl, or each of $R^1$ and $R^2$, and $R^3$ and $R^4$ may, together with the adacent nitrogen form a heterocyclic ring structure. $R^1$, $R^2$, $R^3$ and $R^4$ are never hydrogen, or together with the adjacent nitrogen form the heterocyclic ring structure 1-piperazinyl in this method. As will be recognized, $Z=-(CH_2)_m-NR^1R^2$ in this method and $W=R=$hydrogen in this method. Formula Ia is encompassed by Formula I.

Generally in Method A, an (aryl-, aryloxy-, or arylthio-)alkyl(-halide, -tosylate, or -mesylate) of Formula V is reacted with an alkyldiamine of Formula IV in the presence of a suitable organic solvent (e.g., acetonitrile) followed by reaction with a disubstituted aminoalkylisocyanate (or disubstituted aminoalkylisothiocyanate) of Formula III in a suitable organic solvent (e.g., acetonitrile). The reaction mixture is quenched in water and extracted with a suitable solvent (e.g., methylene chloride) or the mixture is evaporated to dryness and the residue partitioned between water and a suitable organic solvent. The organic layer in any case is dried and evaporated to yield the free base which may or may not crystallize. Pharmaceutically acceptable acid addition salts may then be provided by reacting with a suitable acid. Method A is illustrated more fully in Example 12.

Method B—This method is represented by the following set of equations:

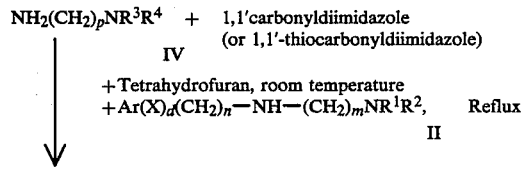

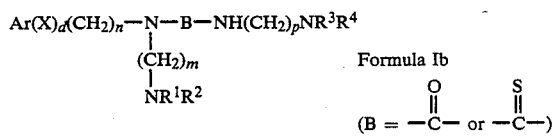

wherein; Ar, X, d, n, m, p, B, $R^1$, $R^2$, $R^3$, $R^4$, Z and W are as defined under Formula Ia. Formula Ib is encompassed by Formula I.

Generally in Method B an alkyldiamine of Formula VI is reacted first with 1,1'-carbonyldiimidazole (or 1,1'-thiocarbonyldiimidazole) in a suitable solvent (e.g., tetrahydrofuran) followd by reaction with an N-[(aryl-, aryloxy-, or arylthio-)alkyl]alkyldiamine of Formula II. The reaction mixtue is quenched in water and extracted with a suitable solvent (e.g., methylene chloride) or the reaction mixture is evaporated to dryness and the residue partitioned between water and a suitable organic solent. The organic layer in any case is dried and evaporated to give the free base which may or may not crystallize. Pharmaceutically acceptable acid addition salts may then be provided with a suitable acid. Method B is illustrated more fully in Example 1.

Method C—This method is represented by the following set of equations:

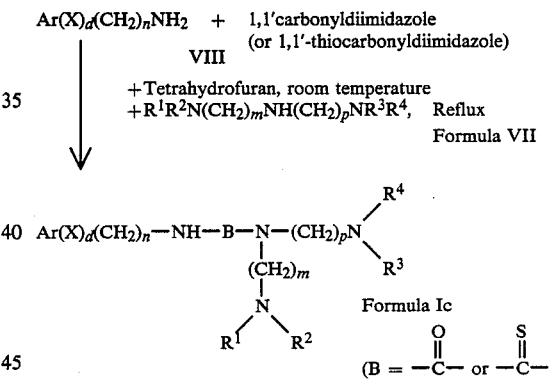

wherein; Ar, X, d, n, m, p, B, $R^1$, $R^2$, $R^3$ and $R^4$ are as defined under Formula Ia. As will be recognized $Z=R=$hydrogen in this method and $W=-(CH_2)_m-NR^1R^2$ in this method. Formula Ic is encompassed by Formula I.

Generally in Method C an (aryl-, aryloxy-, or arylthio-)alkylamine of Formula VIII is reacted with 1,1'-carbonyldiimidazole (or 1,1'-thiocarbonyldiimidazole) in a suitable solvent (e.g., tetrahydrofuran) followed by reaction with a compound of Formula VII. The reaction mixture is stripped of solvents (to dryness) and the residue partitioned between a suitable solvent (e.g., methylene chloride) and water. The free base is obtained by evaporation of the organic layer. Pharmaceutically acceptable acid addition salts may then be provided with a suitable acid. Method C is illustrated more fully in Example 34.

Method D—This method is represented by the following set of equations:

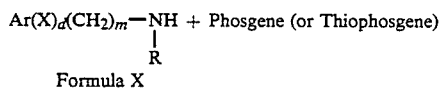

Formula X

+Methylene Chloride
+Base(organic tert-amine base)

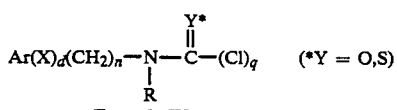

Formula IX

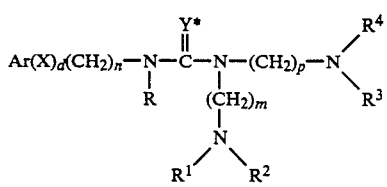

+HN(CH₂)ₘNR¹R²
  (CH₂)ₚNR³R⁴

Formula VII
+Tetrahydrofuran $$Ar(X)_d(CH_2)_n-\underset{R}{N}-\overset{Y^*}{\overset{\|}{C}}-\underset{\underset{\underset{R^1\phantom{xx}R^2}{\diagup\phantom{x}\diagdown}}{N}}{N}-(CH_2)_p-\underset{R^3}{\overset{R^4}{N}}$$
$$\phantom{xxxxxxxxxxxxxxxxxxxx}(CH_2)_m$$

Formula Id wherein; Ar, X, d, n, m, p, R¹, R², R³ and R⁴ are as defined hereinabove under Formula Ia. R is selected from hydrogen, loweralkyl, cycloalkyl, phenyl, phenylloweralkyl, substituted phenyl and substituted phenylloweralkyl. As will be recognized Z=R in this method and W=—(CH₂)ₘ—NR¹R² in this method. When R is hydrogen, q is zero and the dotted line is a double bond forming an isocyanate or isothiocyanate; otherwise the dotted line has no significance. Formula Id is encompassed by Formula I.

Generally in Method D, an (aryl-, aryloxy-, arylthio- or arylsulfonyl)alkylamine of Formula X is reacted with phosgene (or thiophosgene) in a suitable organic solvent (e.g., methylene chloride), plus a tert-amine organic base such as triethylamine, or Proton Sponge ® which is composed of 1,8-bis-(dimethylamino)naphthalene, followed by extraction (washing) with dilute sulfuric acid and the organic layer is dried and evaporated to an oil residue of Formula IX, which may be isolated if desired. The oil is dissolved in appropriate organic solvent (e.g., tetrahydrofuran) and reacted with an appropriate compound of Formula VII. The reaction mixture is stripped of solvents (to dryness) and the residue partitioned between a suitable solvent (e.g., methylene chloride) and water, evaporation of the organic layer yields the free base. Pharmaceutically acceptable acid addition salts may then be provided with a suitable acid. Method D is illustrated more fully in example 19.

Method E—This method is represented by the following set of equations:

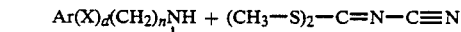

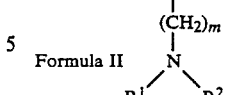

Formula II 24 hr (1) room temperature (2) reflux   (B is C=N—C≡N)

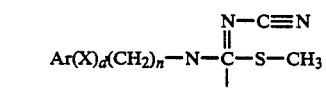

Formula XII

+HN(CH₂)ₚNR³R⁴
  |
  R
XI
+acetonitrile
—2-10 days→

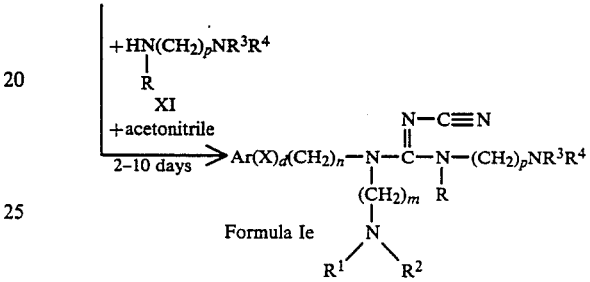

Formula Ie wherein;

Ar, X, d, n, m, p, R¹ and R² are as defined hereinabove under Formula Ia. R, R³ and R⁴ are selected from hydrogen, loweralkyl, cycloalkyl, phenyl, phenylloweralkyl, substituted phenyl, substituted phenylloweralkyl and R³ and R⁴ may form a heterocyclic amine with the adjacent nitrogen atom in this method. With the proviso that when R is not hydrogen, either R is the same as R³, and R⁴ is hydrogen, or R³ and R⁴ may not form the hetrocyclic ring structure 1-piperazinyl. As will be recognized B is cyanoiminomethyl in this method, Z=—(CH₂)ₘ—NR¹R² in this method and W=R in this method. Formula Ie is encompassed by Formula I.

Generally in Method E, an N-[(aryl, aryloxy-, arylthio- or arylsulfonyl-)alkyl]alkyldiamine of Formula II is reacted with dimethyl N-cyanodithioiminocarbonate in a suitable organic solvent (e.g., absolute ethyl alcohol) for approximately 24 hr. The solvent is then evaporated to give a residue, and the residue partitioned between water and a suitable organic solvent (e.g., methylene chloride). Evaporation of the organic layer yields a compound of Formula XII as the free base which may or may not crystallize. The free base of compound of Formula XII is then dissolved in a suitable organic solvent (e.g., acetonitrile) and reacted with an alkyldiamine of Formula XI for 2-10 days. Evaporation of solvent gives an oil residue which is then partitioned between a suitable solvent (e.g., methylene chloride) and water, evaporation of the organic layer in any case gives the free base of the compound of Formula Ie as an oil, which may or may not crystallize. Pharmaceutically acceptable acid addition salts may then be provided with a suitable acid. Method E is illustrated more fully in Preparation 45 and Example 49.

Method F—This method is represented by the following set of equations:

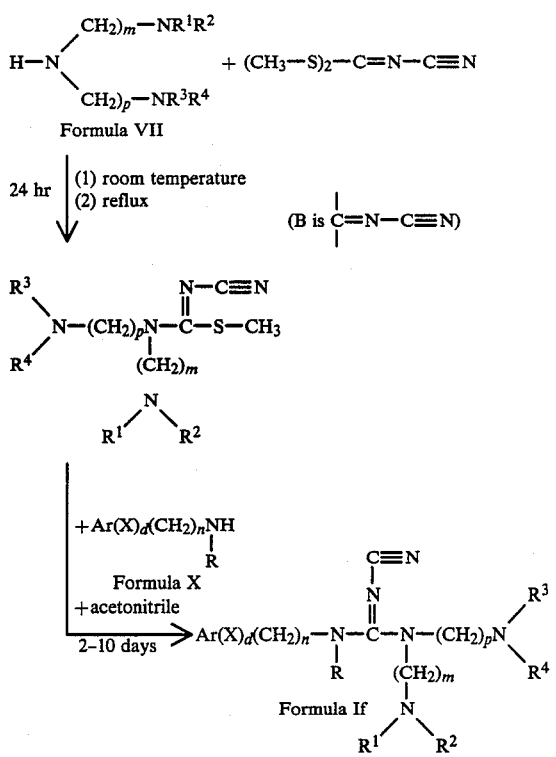

wherein;

Ar, X, d, n, m, p, $R^1$, $R^2$, $R^3$ and $R^4$ are as defined hereinabove under Formula Ia. R is selected from hydrogen, loweralkyl, cycloalkyl, phenyl, phenylloweralkyl, substituted phenyl and substituted phenylloweralkyl in this method, As will be recognized, B is cyanoiminomethyl in this method, Z=R in this method and W=—$(CH_2)_m$—$NR^1R^2$ in this method. Formula If is encompassed by Formula I.

Generally in Method F, a compound of Formula VII is reacted with dimethyl N-cyanodithioiminocarbonate in a suitable organic solvent (e.g., absolute ethyl alcohol) for approximately 24 hr, the solvent is then evaporated to give a residue and the residue partitioned between water and a suitable organic solvent (e.g., methylene chloride). Evaporation of the organic layer yields a compound of Formula XIII as the free base which may or may not crystallize. The free base of compound of Formua XIII is dissolved in a suitable organic solvent (e.g., acetonitrile) and reacted with an (aryl-, aryloxy-, or arylthio-)alkylamine of Formula X for 2-10 days. Evaporation of solvent gives an oil residue which is then partitioned between organic solvent (e.g., methylene chloride) and water, evaporation of the organic layer in any event gives the free base of the compound of Formula If as an oil, which may or may not crystallize. Pharmacuetically acceptable acid addition salts may be provided with a suitable acid. Method F is illustrated more fully in Example 52.

Some of the starting compounds of the formula:

are available commercially. Some of these wherein $(X)_d$ is sulfur were prepared from metal salts of arylsulfides and α,ω-dihaloalkyl compounds in refluxing alcohol as representd by the following formula:

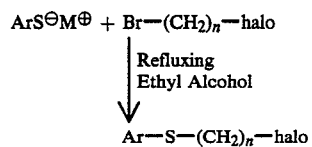

alternately, the chloro starting analogs wre prepared from arylsulfides and Cl—$(CH_2)_n$—OH, followed by reaction with thionyl chloride as represented by the following equations:

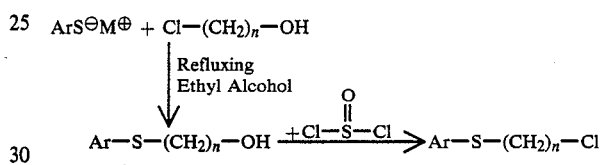

The sulfinyl and sulfonyl starting compounds of Formula V are obtained by oxidation with hydrogen peroxide in acetic acid as follows:

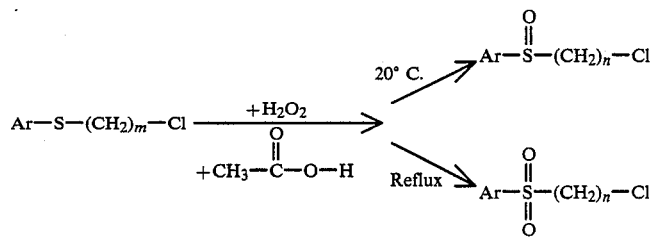

The precursor arlysulfides of the compounds of Formula V may be purchased or prepared as illustrated by the following equation, Method of Organic Synthesis 51, 139-142:

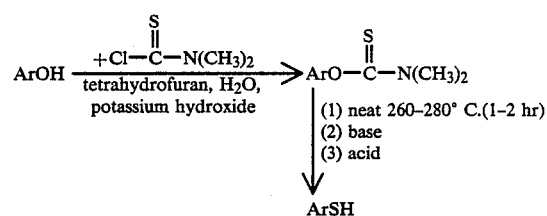

Compounds of Formula V wherein $(X)_d$ is oxygen may be prepared from hydroxy substituted aryl compounds and α,ω-dihaloalkyl compounds in sodium hydroxide as represented by the following equation:

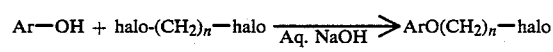

or alternatively, by reaction of an appropriate sodium aryloxide with an appropriate ω-chloroalcohol followed by reaction with thionyl chloride as represented by the following equation:

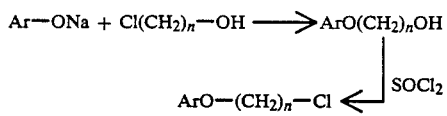

Starting compounds of Formula III are available commercially or may be prepared as illustrated by the following equation:

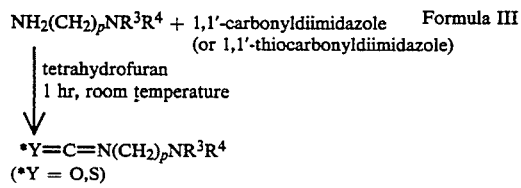

Starting compounds of Formula VIII may be prepared as illustrated by the following equations:

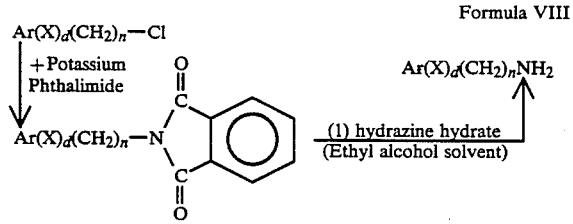

The starting compounds of Formula VII can be prepared by the method of Yeakey, E. L. et al. as disclosed in Ger. Offen. 3,048,832. The procedure is outlined by the following set of equations showing dehydrogeneration of the appropriate alkyldiamine or hydrogenation of the appropriate nitrile.

wherein $R^1, R^2, R^3$ and $R^4$ are as defined hereinabove under Formula I except hydrogen, and m and p are as defined under Formula I.

The starting compounds of Formula X may be prepared as illustrated by the following equation:

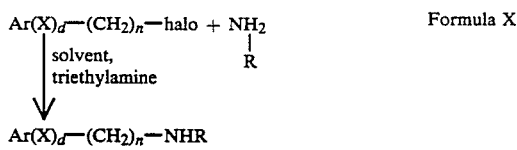

Alternately, the sulfinyl and sulfonyl starting compounds of Formula X may be prepared by reaction of an arylthioalkylhalide compound of Formula V with an appropriate amine, and by further reaction with sodium perborate, as illustrated by the following equations:

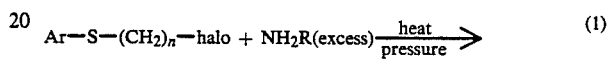 (1)

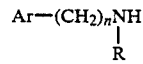

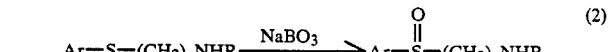 (2)

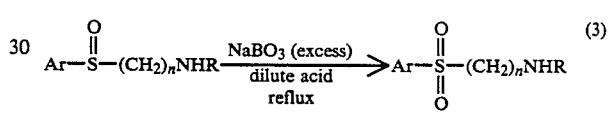 (3)

wherein Ar, R and n are as defined under Formula I. Reaction (1) is carried out by heating the reactants in a closed container such as a bomb. Reaction (2) is carried out at room temperature and reaction (3) is conducted at reflux. Reaction (2) as a step may be omitted by going directly to excess sodium perborate at reflux temperature.

Starting compounds of Formula X wherein $(X)_d$ is sulfonyl may also be prepared by reacting an appropri-

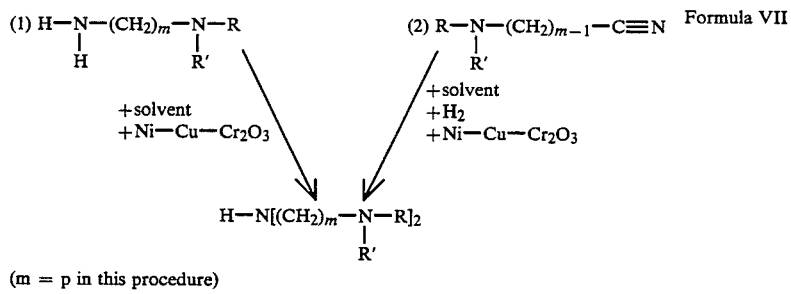

(m = p in this procedure)

Alternately, the starting compounds of Formula VII may be prepared as illustrated by the following equation:

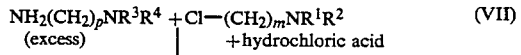

ate arylthioalkylamine with phenyl chloroformate, followed by reaction with m-chloroperpoxybenoic acid and hydrolysis with hydrobromic acid. The equations are:

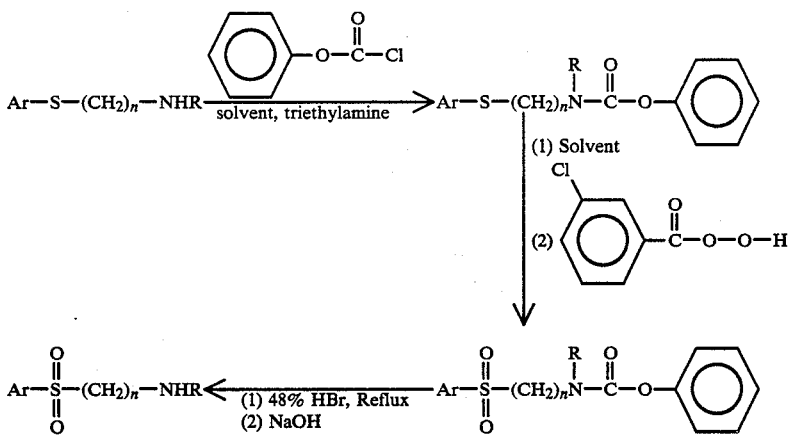

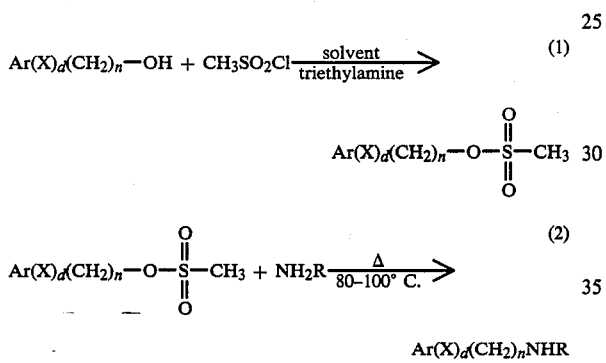

Starting compounds of Formula X wherein $(X)_d$ is oxygen, thio, sulfonyl or when d is zero may be prepared via mesyl derivatives as illustrated by the following equations:

$$Ar(X)_d(CH_2)_n-OH + CH_3SO_2Cl \xrightarrow[\text{triethylamine}]{\text{solvent}} \quad (1)$$

$$Ar(X)_d(CH_2)_n-O-\underset{\underset{O}{\|}}{\overset{\overset{O}{\|}}{S}}-CH_3 \quad 30$$

$$Ar(X)_d(CH_2)_n-O-\underset{\underset{O}{\|}}{\overset{\overset{O}{\|}}{S}}-CH_3 + NH_2R \xrightarrow{\Delta}{80-100°\,C.} \quad (2)$$

$$Ar(X)_d(CH_2)_nNHR$$

wherein Ar, X, d and n are defined under formula I except X is not sulfinyl in this method.

Optionally, compounds of Formula I wherein nitrogen is substituted by benzyl (i.e., —CH₂—Phenyl) may be hydrogenated over paladium; for example,

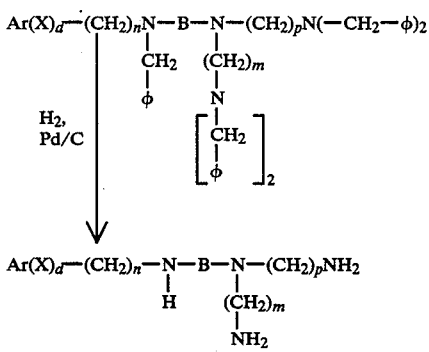

with the provisos $(X)_d$ is other than thio or sulfinyl, and B is other than thioxomethyl, and Ar is not phenyl substituted by loweralkylthio or loweralkylsulfinyl.

Optionally, compounds of Formula I wherein the —NR¹R² or —NR³R⁴ groups form a heterocyclic ring structure selected from 4-loweralkoxycarbonyl-1-piperazinyl, 4-phenylmethyloxycarbonyl-1-piperazinyl or 4-benzyl-1-piperazinyl may be hydrogenated over paladium on carbon for example,

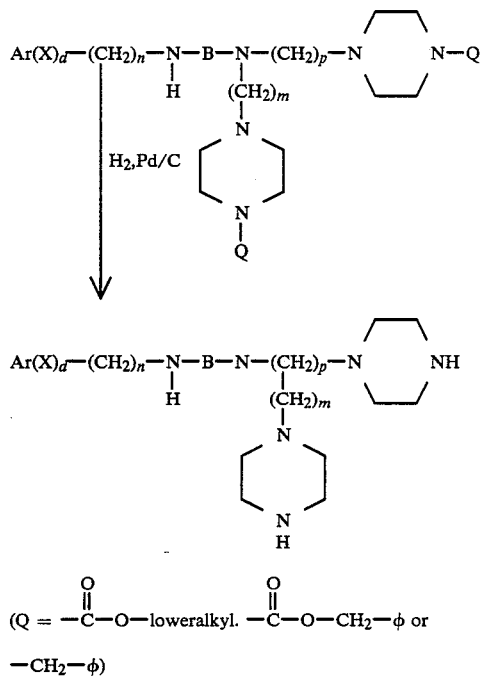

(Q = $-\overset{\overset{O}{\|}}{C}-O-$loweralkyl, $-\overset{\overset{O}{\|}}{C}-O-CH_2-\phi$ or $-CH_2-\phi$)

with the provisos $(X)_d$ is other than thio or sulfinyl, and B is other than thioxomethyl and Ar is not phenyl substituted by loweralkylthio or loweralkylsulfinyl.

The preparation of chemical intermediates is illustrated in the following preparations 1–50. Examples 1–64 illustrate the synthesis methods for preparing compounds of Formula I. The scope of the invention is not limited by the descriptive methods and procedures of the preparations and examples however.

Preparation 1

N,N-Diethyl-N′-[2-(phenylsulfonyl)ethyl]-1,3-propanediamine hydrochloride [1:2]

A solution of [2-chloroethyl)sulfonyl]benzene (50.0 g, 0.244 mole) in 500 ml of acetonitrile was prepared. To this solution was added triethylamine (24.6 g, 0.244 mole). The solution was cooled in an ice bath, and a solution of N,N-diethyl-1,3-propanediamine (31.8 g, 0.244 mole) in acetonitrile was added. The resulting solution was stirred overnight at room temperature.

The reaction mixture was filtered and stripped to dryness. The resulting oil was dissolved in methylene chloride and the solvent was extracted with water. The methylene chloride layer was extracted with 1N sulfuric acid, and the acidic layer was made alkaline and extracted with methylene chloride. The methylene chloride was stripped and the resulting oil was partitioned six times between diethyl ether and water. The oil obtained after removal of diethyl ether was converted to the dihydrochloride salt and the salt was recrystallized from methanol-diethyl ether to give 4.69 g (5.2%) of white crystalline product, mp 149°–154° C.

**The low yield is due to the high solubility of the product in water.

Analysis: Calculated for $C_{15}H_{28}N_2O_2SCl_2$: C, 48.51; H, 7.60; N, 7.54. Found: C, 48.48; H, 7.60; N, 7.44.

Preparation 2

N,N-Diethyl-N'-[2-(phenylsulfonyl)ethyl]-1,2-ethanediamine maleate [1:2]

A solution of 52.29 g (0.256 mole) of [(2-chloroethyl)-sulfonyl]benzene and 35 g (0.302 mole) of diethylaminoethylamine is a mixture of 30 ml of triethylamine and 800 ml of acetonitrile was stirred at room temperature for 44 hr. The solvent was removed in vacuo and the residue was partitioned between methylene chloride and dilute sodium hydroxide. The methylene chloride solution was extracted with water and was dried over magnesium sulfate. The solvent was removed in vacuo to give the free base of the title compound as an oil. This was converted to the dimaleate salt and the salt was recrystallized from methanol/diethyl ether to give 114.51 g (86.7%) of title compound, a white crystalline solid; mp 144°–145° C.

Analysis: Calculated for $C_{22}H_{32}N_2SO_{10}$: C, 51.15; H, 6.24; N, 5.42. Found: C, 50.98; H, 6.24; N, 5.36.

Preparation 3

N,N-Dimethyl-N'-[2-(phenylsulfonyl)ethyl]-1,2-ethanediamine maleate [1:2]

A mixture of 34.62 g (0.169 mole) of [2-chloroethyl)-sulfonyl]benzene 17.96 g (0.204 mole) of N,N-dimethylethylenediamine and 20.0 g (0.198 mole) of triethylamine in 600 ml of acetonitrile was stirred at room temperature overnight. The solvent was removed in vacuo, and the residue was partitioned between methylene chloride and dilute sodium hydroxide. The methylene chloride solution was dried over magnesium sulfate, and the solvent was removed in vacuo. The residue was dissolved in 1 liter of methanol, and a solution of 39.44 g (0.34 mole) of maleic acid in 200 ml of hot methanol was added. A white precipitate was collected at room temperature to give 63.72 g (77.2%) of title compound, a white crystalline soid; mp 158°–159° C.

Analysis: Calculated for $C_{20}H_{28}N_2O_{10}S$: C, 49.17; H, 5.78; N, 5.73. Found: C, 49.19; H, 5.72; N, 5.83.

Preparation 4

N-[2-(Phenylsulfonyl)ethyl]-1-pyrrolidineethanamine maleate [1:2]

A mixture of 35.00 g (0.171 mole) of [2-chloroethyl)-sulfonyl]benzene, 19.8 g (0.173 mole) of N-(2-aminoethyl)pyrrolidine and 20.0 g (0.198 mole) of triethylamine in 800 ml of acetonitrile was stirred at room temperature for 16 hr. The solvent was removed in vacuo, and the residue was partitioned between methylene chloride and dilute sodium hydroxide. The methylene chloride solution was dried over magnesium sulfate and the solvent was removed in vacuo to give an oil. This was dissolved in 1 liter of methanol, a solution of 40 g (0.345 mole) of maleic acid in 800 ml of methanol was added, and a precipitate formed at room temperature to give 43.21 g (49.1%) of title compound, a white crystalline solid, mp 149°–151° C.

Analysis: Calculated for $C_{22}H_{30}N_2O_{10}S$: C, 51.35; H, 5.88; N, 5.44. Found: C, 51.62; H, 5.80; N, 5.54.

Preparation 5

N-[2-(Phenylsulfonyl)ethyl]-1-piperidineethanamine maleate [1:2]

A mixture of 40.94 g (0.20 mole) of [(2-chloroethyl)-sulfonyl]benzene, 27.85 g (0.217 mole) of N-(2-aminoethyl)piperidine and 28.0 g (0.277 mole) of triethylamine in 800 ml of acetonitrile was stirred at room temperature overnight. The solvent was removed in vacuo, and the residue was partitioned between methylene chloride and dilute sodium hydroxide. The methylene chloride solution was dried over magnesium sulfate, and the solvent was removed in vacuo. The residue was dissolved in methanol, a solution of 2 equivalents of maleic acid in methanol was added, and the product crystallized from the solution at room temperatue to give 64.35 g (60.78%) of title compound as a white crystalline solid, mp 154°–155.5° C.

Analysis: Calculated for $C_{23}H_{32}N_2O_{10}S$: C, 52.26; H, 6.10; N, 5.30. Found: C, 52.46; H, 6.05; N, 5.39.

Preparation 6

N-[2-(Phenylsulfonyl)ethyl]-4-morpholineethanamine maleate [1:2]

A solution of 53.20 g (0.260 mole) of [2-chloroethyl)-sulfonyl]benzene, 36.56 g (0.281 mole) of N-(2-aminoethyl)morpholine and 31 g (0.307 mole) of triethylamine in 800 ml of acetonitrile was stirred at room temperature for 18 hr. The solvent was removed in vacuo and the residue was partitioned between methylene chloride and dilute sodium hydroxide. The solvent was removed from the methylene chloride solution, and the residue was dissolved in diethyl ether. The diethyl ether solution was extracted with water. The aqueous extract was extracted with methylene chloride. The methylene chloride extract was dried over magnesium sulfate, and the solvent was removed in vacuo to give 59.6 g of the free base of the title compound, an oil. This was converted to the dimaleate salt, and the salt was crystallized from methanol to give 92.88 g (67.3%) of the title compound, a white crystalline solid; mp 172°–173° C. with decomposition.

Analysis: Calculated for $C_{22}H_{30}N_2O_{11}S$: C, 49.81; H, 5.70; N, 5.28. Found: C, 50.02; H, 5.70; N, 5.28.

Preparation 7

N-[2-(Phenylsulfonyl)ethyl]-1-homopiperidineethanamine maleate [1:2]

A mixture of 20.06 g (0.098 mole) of [(2-chloroethyl)-sulfonyl]benzene 15.44 g (0.109 mole) of N-(2-aminoethyl)homopiperidine, and 15.0 g (0.149 mole) of triethylamine in 800 ml of acetonitrile was stirred at room temperature for 18 hr. The solvent was removed in vacuo, and the residue was partitioned between methylene chloride and water. The methylene chloride solution was dried over magnesuim sulfate, and the solvent waas removed in vacuo to give an oil. This was dissolved in methanol, and the solution was treated with a solution of 2 equivalents of maleic acid (25.52 g, 0.22 mole) in methanol. A white solid precipitated at room temperature to give 32.3 g (60.7%) of title compound as a white solid; mp 144°–146° C.

Analysis: Calculated for $C_{24}H_{34}N_2O_{10}S$: C, 53.13; H, 6.32; N, 5.16. Found: C, 52.98; H, 6.26; N, 5.14.

Preparation 8

N-Methyl-N-phenyl-N'-[2-(phenylsulfonyl)ethyl]-1,2-ethanediamine maleate [1:1]

A solution of 34.7 g (0.170 mole) of [(2-chloroethyl)sulfonyl]benzene, 25.0 g (0.167 mole) of N-(2-aminoethyl)-N-methylaniline and 22.0 g (0.22 mole) of triethylamine in 800 ml of acetonitrile was stirred at room temperature for 18 hr. The solvent was removed in vacuo, and the residue was partitioned between methylene chloride and dilute sodium hydroxide. The methylene chloride solution was extracted with dilute sulfuric acid, and a white precipitate was collected. The acidic extract was made basic with an excess of sodium hydroxide, and the basic solution was extracted with methylene chloride. The methylene chloride solution was dried over magnesium sulfate, and the solvent was removed in vacuo to give 15.45 g (28.7%) of the free base of the title compound, an oil.

The white solid (above) was treated with an excess of dilute sodium hydroxide solution and the aqueous mixture was extracted with methylene chloride. The methylene chloride solution was dried over magnesium sulfate, and the solvent was removed in vacuo to give 14.26 g (26.9%) of the free base of title compound as an oil.

The two samples of the free base of title compound were combined and the material was converted to the maleate salt. The salt was recrystallized from methanol-ether to give 37.3 g (51.5%) of title compound as a white, crystalline solid, mp 149.5°–151° C.

Analysis: Calculated for $C_{21}H_{26}N_2O_6S$: C, 58.05; H, 6.03; N, 6.45. Found: C, 57.81; H, 6.03; N, 6.35.

Preparation 9

N,N-Diethyl-N'-(2-phenoxyethyl)-1,2-ethanediamine maleate [1:2]

A mixture of 141.56 g (0.704 mole) of β-bromophenetole and 115.8 g (0.998 mole) of N,N-diethylethylenediamine in 1 liter of acetonitrile was refluxed for 20 hours. The solvent was removed in vacuo, and the residue was partitioned between methylene chloride and dilute sodium hydroxide. The methylene chloride solution was dried over magnesium sulfate, and the solvent was removed in vacuo to give 148.95 g (89.7%) of the free base of the title compound, a light brown liquid. Part of this was converted to the dimaleate salt, and the salt was recrystallized from methanol-ether to give the title compound as a white crystalline solid, mp 129.5°–131° C.

Analysis: Calculated for $C_{22}H_{32}N_2O_9$: C, 56.40; H, 6.89; N, 5.98. Found: C, 56.12; H, 6.96; N, 6.00.

Preparation 10

N,N-Diethyl-N'-[2-(phenylthio)ethyl]-1,2-ethanediamine maleate [1:2]

A mixture of 60.24 g (0.350 mole) of [(2-chloroethyl)thio]benzene, 84 g (0.72 mole) of N,N-diethylethylenediamine, and 80.0 g (0.75 mole) of sodium carbonate in 1.5 liters of acetonitrile was refluxed for 16 hr. The solvent was removed in vacuo, and the residue was partitioned between methylene chloride and dilute sodium hydroxide. The methylene chloride solution was dried over sodium sulfate, and the solvent was removed in vacuo to give an oil. This was dissolved in 800 ml of methanol. A solution of approximately 2 equivalents of maleic acid in methanol was added followed by the addition of anhydrous diethyl ether until the solution became slightly cloudy. A white solid precipitated at −5° C. to give 73.15 g (43.2%) of title compound, a white crystalline solid, mp 131°–133° C.

Analysis: Calculated for $C_{22}H_{32}N_2O_8$: C, 54.53; H, 6.66; N, 5.71. Found: C, 54.27; H, 6.68; N, 5.73.

Preparation 11

N,N-Diethyl-N'-(3-phenylpropyl)-1,2-ethanediamine oxalate hydrate [1:2:0.5]

A mixture of 71.5 g (0.359 mole) of 3-bromo-1-phenylpropane, 82.0 g (0.707 mole) of N,N-diethylethylenediamine and excess sodium carbonate in 1 liter of acetonitrile was refluxed for 16 hr. The solvent was removed in vacuo, and the residue was partitioned between methylene chloride and diluted sodium hydroxide solution. The methylene chloride solution was dried over sodium sulfate, and the solvent was removed in vacuo to give an oil. This was dissolved in 1.5 liters of methanol, and a solution of 67.5 g (0.75 mole of oxalic acid in methanol was added. A white solid precipitated at room temperature to give 108.88 g (71.6%) of title compound, a white crystalline solid, mp 209°–211° C. with decomposition.

Analysis: Calculated for $C_{19}H_{31}N_2O_{8.5}$: C, 53.89; H, 7.38; N, 6.62. Found C, 54.23; H, 7.36; N, 6.89.

Preparation 12

N,N-Diethyl-N'-[2-(phenylsulfinyl)ethyl]-1,2-ethanediamine maleate [1:2]

A mixture of 20.0 g (0.106 mole) of [(2-chloroethyl)sulfinyl]benzene, 30.0 g (0.259 mole) of N,N-diethylethylenediamine and excess sodium carbonate in 600 ml of acetonitrile was refluxed for 16 hr. The reaction mixture solution was filtered, and the solvent was removed in vacuo. The residue was partitioned between methylene chloride and dilute sodium hydroxide. The methylene chloride solution was dried over sodium sulfate and the solvent was removed in vacuo to give an oil. This was dissolved in methanol, and a solution of 2 equivalents of maleic acid in methanol was added. Diethyl ether was added and a whie solid precipitated to give 26.7 g (50.3%) of title compound, a white crystalline solid, mp 111°–112.5° C.

Analysis: Calculated for $C_{22}H_{32}N_2O_9S$: C, 52.79; H, 6.44; N, 5.60. Found: C, 52.48; H, 6.49; N, 5.57.

Preparation 13

N,N-Diethyl-N'-[2-(phenylsulfonyl)ethyl]-1,4-butanediamine oxalate hydrate [1:2:0.5]

A mixture of 28.2 g (0.138 mole) of [(2-chloroethyl)sulfonyl]benzene and 20.0 g (0.139 mole) of 4-(N,N-diethylamino)-1-butanamine in 700 ml of acetonitrile was stirred at room temperature for 16 hr. The solvent was removed in vacuo, and the residue was partitioned between methylene chloride and dilute sodium hydroxide. The methylene chloride solution was dried over magnesium sulfate, and the solvent was removed in vacuo. The residue was dissolved in methanol, a solution of 25.0 g (0.278 mole) of oxalic acid was added and a precipitate was collected to give 47.69 g (68.9%) of title compound, a white crystalline solid, mp 158°–165° C. with decomposition.

Analysis: Calculated for $C_{20}H_{33}N_2O_{10.5}S$: C, 47.90; H, 6.63; N, 5.59. Found: C, 48.09; H, 6.44; N, 5.49.

Preparation 14

1-Methyl-N-[2-(2-naphthalenylthio)ethyl]ethanamine hydrochloride [1:1]

2-Naphthalenethiol was prepared by the method of Org. Syn. 51, PP 139–142.

A solution of the potassium salt of 2-naphthalenethiol was pepared by reacting 50.89 g (0.32 mole) of 2-naphthalenethiol and 17.92 g (0.32 mole) of potassium hydroxide in 500 ml ethanol. To the solution was added 297.6 g (1.6 mole) of 1,2-dibromoethane. The solution was refluxed overnight, stripped to dryness and the residue dissolved in chloroform. The chloroform layer was extracted with water and 10% sodium hydroxide. The chloroform layer was evaporated to leave a dark-brown oil as residue which contained about 20% of an unwanted dimer: 1,2-bis naphthalenylthioethane. The impure mixture was stirred overnight with 100 ml of isopropylamine. The reaction mixture was evaporated to dryness and the residue partitioned between chloroform and water. Evaporation of the chloroform layer gave an oil. The oil was triturated with methanol and chilled, and a precipitate was filtered off which proved to be the dimer: 1,2-bis-(2-thionaphthylene)ethane. The filtrate was treated with ethereal hydrogen chdloride to give the title salt as white crystals weighing 10.2 g (11.3%), m.p. 137.5°–138.5° C.

Analysis: Calculated for $C_{15}H_{20}NSCl$: C, 63.92; H, 7.15; N, 4.97. Found: C, 63.99; H, 7.20; N, 5.10.

Preparation 15

N-[2-[(2,3-Dihydro-1H-inden-4-yl)sulfonyl]ethyl]-1-methyl-ethanamine, and

N-[2-[(2,3-Dihydro-1H-inden-5-yl-sulfonyl]ethyl]-1-methyl-ethanamine 2-(2,3-Dihydro-1H-indene-4-yl-thiol and 2-(2,3-dihydro-1H-indene-5-yl thiol are first prepared by the method of Org. Syn. 51, pp 139–142 used for the preparation of 2-naphthalenethiol.

From these thiols are prepared:

1-Methyl-N-[2-(4-indanethio)ethyl]ethanamine and 1-methyl-N-[2-(5-indanethio)ethyl]ethanamine, utilizing the method of Preparation 14. The title compounds are prepared therefrom by hot oxidation with sodium perborate, wherein compounds are in dilute acid solutions and refluxed with excess sodium perborate for approximately 6–12 hr. The reaction mixtures are then cooled in ice and made alkaline with sodium hydroxide and extracted with an appropriate organic solvent (e.g., chloroform). Evaporation of the organic solvent leaves the title compounds as free bases.

Preparation 16

1-Methyl-N-[2-[(4-nitrophenyl)sulfonyl]ethyl]ethanamine

A solution of 2-chloroethyl-4-nitrophenylsulfone in isopropylamine is stirred at room temperature for about 72 hr. The isopropylamine is removed by evaporation, and the residue is dissolved with agitation in a mixture of methylene chloride and dilute sodium hydroxide. The methylene chloride layer is extracted with dilute sodium hydroxide, and dried over magnesium sulfate. The solvent is removed by evaporation to give 1-methyl-N-[2-[(4-nitrophenyl)sulfonyl]ethyl]ethanamine as an oil.

Preparation 17

1-Methyl-N-[2-[(4-methylphenyl)thio]ethyl]ethanamine hydrochloride [1:1]

A solution of 10 g (0.035 mole) of 1-p-thiocresyl-2-methanesulfonyl ethane in 50 ml of isopropylamine was heated at 100° C. overnight in a bomb. The reaction mixture was cooled to room temperature and stripped to dryness. The resulting oil residue was dissolved in chloroform and the solution extracted with 1N sulfuric acid. The acidic layer was carefully basified with 50% aqueous sodium hydroxide and extracted with chloroform. Evaporation of chloroform gave an oil, the free base of the title compound. The oil was reacted with ethereal hydrogen chloride, and the salt obtained was recrystallized from methanol-diethyl ether to give 4.5 g (53.1%) of white crystalline solid, m.p. 146°–147° C.

Analysis: Calculated for $C_{12}H_{20}SNCl$: C, 58.64; H, 8.20; N, 5.70. Found: C, 58.64; H, 8.29, N, 5.71.

Preparation 18

N-[2-[(2-Furanylmethyl)thio]ethyl]-2-propanamine hydrochloride

A solution of 2-chloroethyl-2-furanylmethyl sulfide in isopropylamine is agitated 8–12 hr in a stainless steel bomb at 80° C. The reaction mixture is then stripped to dryness and the residue is partitioned between water and chloroform. The chloroform layer is extracted with 1N sulfuric acid; whereupon two layers are obtained: a water phase (upper), and a chloroform phase (lower). The aqueous phase is made alkaline and extracted with chloroform. Evaporation of the organic layer yields the free base of the title compound, which is reacted with ethereal hydrogen chloride to give the hydrochloride salt which is then recrystallized from methanol/diethyl ether.

Preparation 19

N-[2-[(2-Furanylmethyl)sulfonyl]ethyl]-2-propanamine

A solution of 2-chloroethyl-2-furanylmethyl sulfone in isopropylamine is stirred at room temperature for about 72 hr. The isopropylamine is removed by evaporation and the residue is dissolved with agitation in a mixture of methylene chloride and dilute sodium hydroxide. The methylene chloride layer is extracted with dilute sodium hydroxide and dried over magnesium sulfate. The solvent is removed by evaporation to give the free base of the title compound, which is converted to the hydrochloride salt and is then recrystallized from methanol-diethyl ether.

Preparation 20

N-[2-[(2-Furanylmethyl)sulfinyl]ethyl]-2-propanamine

A solution of N-[(2-furanylmethyl)thio]ethyl]-2-propanamine and sodium perborate in 1M sulfuric acid is stirred at room temperature for about 18 hr. The solution is made basic with 50% sodium hydroxide and the basic solution extracted with methylene chloride. The methylene chloride layer is dried with magnesium sulfate, and the solvent removed in vacuo to give a solid which is then recrystallized from ether-hexane to give the free base title compound.

Preparation 21

1-Methyl-N-[2-(phenylsulfonyl)ethyl]ethanamine hydrochloride [1:1]

A solution of 49.63 g (0.24 mole) of 2-chloroethylphenyl sulfone in 300 ml of isopropylamine was stirred at room temperature for about 20 hr. The isopropylamine was removed in vacuo and the residue was dissolved with agitation in a mixture of methylene chloride and dilute sodium hydroxide. The methylene chloride layer was extracted several times with dilute sodium hydroxide and dried over magnesium sulfate. The solvent was removed in vacuo to give 55.1 g of oil, the free base of the title compound. A portion of the oil was converted to the hydrochloride salt with ethereal hydrogen chloride and was recrystallized from methanol-diethyl ether to give white crystals, m.p. 151°-152.5° C.

Analysis: Calculated for $C_{11}H_{18}NO_2SCl$: C, 50.09, H, 6.88; N, 5.31. Found: C, 50.12; H, 6.91; N, 5.31.

Preparation 22

N-[2-[(4-Dimethylaminophenyl)sulfonyl]ethyl]-2-propanamine

2-Chloroethyl 4-dimethylaminophenyl sulfone is reacted as in Preparation 19 with isopropylamine to give the title compound.

Preparation 23

N-[2-[(4-Chlorophenyl)sulfonyl]ethyl]-1-methylethanamine hydrochloride [1:1]

A solution of 51.51 g (0.216 mole) of 2-chloroethyl p-chlorophenyl sulfone in 400 ml of isopropylamine was stirred at room temperature for about 72 hr. The isopropylamine was removed in vacuo, and the residue was dissolved with agitation in a mixture of methylene chloride and dilute sodium hydroxide. The methylene chloride layer was extracted several times with dilute sodium hydroxide and dried over magnesium sulfate. The solvent was remaoved in vacuo to give 53.5 g oil, the free base of the title compound. A portion of the oil was converted to the hydrochloride salt which was recrystallized from methanol-diethyl ether to give a white crystalline solid, m.p. 169°-170° C.

Analysis: Calculated for $C_{11}H_{17}NO_2SCl_2$: C, 44.30; H, 5.75; N, 4.70. Found: C, 44.37; H, 5.81; N, 4.73.

Preparation 24

N-[2-[(4-Ethoxyphenyl)sulfonyl]ethyl]-2-propanamine hydrochloride [1:1]

To a suspension of 6.6 g of a 60% dispersion of sodium hydride in oil (0.165 mole) in 300 mole of dimethyl sulfoxide was added 7.5 g (0.163 mole) of absolute ethanol. The mixture was stirred at room temperature for 0.5 hr, and 20.8 g (0.080 mole) of N-[2-(4-chlorophenylsulfonyl)ethyl]-2-propanamine hydrochloride (obtained in Preparation 23) was added as a solid. The mixture was heated at 120°-140° C. for 1 hr, and the solvent was removed in vacuo. The residue was partitioned between methylene chloride and dilute sodium hydroxide. The methylene chloride solution was dried over magnesium sulfate, and the solvent removed in vacuo. The residue was dissolved in methanol, an excess of ethereal hydrogen chloride was added, and ether was added. A white solid precipitated in amount of 14.92 g (69.2%), m.p. 168°-170° C.

Analysis: Calculated for $C_{13}H_{22}NO_3SCl$: C, 50.72; H, 7.20; N, 4.55. Found: C, 50.73; H, 7.31; N, 4.59.

Preparation 25

N-[2-[(4-Methoxyphenyl)sulfonyl]ethyl]-2-propanamine hydrochloride [1:1]

A solution of 16.46 g (0.055 mole) of N-[2-[(4-chlorophenyl)sulfonyl]ethyl-1-methyl ethanamine hydrochloride (obtained in Preparation 23) and 16.2 g (0.3 mole) of sodium methylate in 500 ml of dimethylsulfoxide was heated at 95° C. for 2 hr with stirring. The solvent was removed on a rotary evaporator at reduced pressure and the residue was partitioned between water and chloroform. The aqueous phase was made strongly alkaline with 50% sodium hydroxide and extracted with chloroform. The chloroform layers were combined and evaporated to leave an oil. The oil was reacted with ethereal hydrogen chloride. Recrystallization of the salt from methanol-diethyl ether gave 9.11 g (56.4%) of white crystalline product, m.p. 142°-145° C.

Analysis: Calculated for $C_{12}H_{20}NO_3SCl$: C, 49.06; H, 6.86; N, 4.77. Found: C, 48.98; H, 6.91; N, 4.80.

Preparation 26

N-[2-(3,4-Dichlorophenoxy)ethyl]-N-1-methylethanamine hydrochloride [1:1]

A solution of 36.18 g (0.135 mole) of 2-bromoethyl-3,4-dichlorophenyl ether and 31.8 g (0.54 mole) of isopropylamine in 200 ml of chloroform was heated at reflux for 72 hours. Solvent was removed in a rotary evaporator, and the residue partitioned between water and chloroform. The chloroform layer was extracted with 1N sulfuric acid. The aqueous phase, which contained a dispersed white solid, was made alkaline with 10% aqueous sodium hydroxide and extracted with chloroform. The chloroform layer was concentrated under vacuum to an oil, the free base. A portion of the oil was dissolved in methanol and the solution was treated with ethereal hydrogen chloride. The precipitate was recrystallized from methanol-diethyl ether. Overall yield of white crystalline product was 62.4% of theory based on the proportion taken. The melting point was 186°-187° C.

Analysis: Calculated for $C_{11}H_{15}NOCl_3$: C, 46.42; H, 5.67; N, 4.92. Found: C, 46.53; H, 5.69; N, 5.00.

Preparation 27

Part A

Methanesulfonic acid[2-[(3,4-dichlorophenyl)thio]ethyl]ester

A solution of 2-[(3,4-dichlorophenyl)thio]ethanol (117.97 g, 0.53 mole) prepared from 3,4-dichlorothiophenol and 2-chloroethanol, in benzene (500 ml) with triethylamine (53.5 g, 0.53 mole) was prepared. To this solution was added dropwise a benzene solution of methanesulfonyl chloride (60.9 g, 0.53 mole) over 1 hr (in an ice bath). The reaction mixture was stirred at room temperature overnight and then filtered. Solvent was removed by evaporation to give an oil which crystallized. A 5 g portion was recrystallized from isopropyl ether to give 4.61 g (47.9% yield based on aliquot) of white crystalline solid, m.p. 53°-55° C.

Analysis: Calculated for $C_9H_{10}S_2O_3Cl_2$: C, 35.89; H, 3.35. Found: C, 35.81; H, 3.43.

Part B

N-[2-[(3,4-dichlorophenyl)thio]ethyl]-2-propanamine hydrochloride [1:1]

A solution of methanesulfonic acid [2-[(3,4-dichlorophenyl)thio]ethyl]ester (obtained in Part A of this preparation, 151.46 g, 0.548 mole) in 100 ml of isopropylamine was heated overnight in a bomb at 100° C. The isopropylamine was removed by rotary evaporation, and the residue partitioned between chloroform and 5% sodium hydroxide. The chloroform was removed by rotary evaporation to give a clear oil. The oil was dissolved in methanol and converted to the hydrochloride salt. Recrystallization from methanoldiethyl ether gave 101.53 g (0.3376 mole, 61.6% yield) of white crystalline product, m.p. 132°–133.5° C.

Analysis: Calculated for $C_{11}H_{16}NSCl_3$: C, 43.94; H, 5.36; N, 4.66. Found: C, 44.09; H, 5.34; N, 4.79.

Preparation 28

2-Pyridineethanamine, hydrochloride [1:2]

Concentrated hydrochloric acid (16.50 ml, 0.20 mole) was poured slowly into a stirred solution of 2-(2-aminoethyl)pyridine (12.22 g, 0.10 mole) in 200 ml absolute ethanol. The mixture was concentrated to dryness and the residual solid recrystallized from 600 ml absolute ethanol. The light orange-pink solid was collected and yielded 8.48 g; mp 187°–189° C. (lit[1] 186°–189° C.).

References:
[1] J. Am. Chem. Soc. 74, 614. Several additional literature values are reported; J. Org. Chem. 14, 388–93; mp 189° C. J. Am. Chem Soc. 79, 2811–14; mp 182°–188° C. J. Am. Chem. Soc. 82, 441; mp 206°–207° C. J. Am. Chem. Soc. 63, 2771; mp 185°–189° C.

Analysis: Calculated for $C_7H_{12}N_2Cl_2$: C, 43.10; H, 6.20; N, 14.36. Found: C, 43.05; H, 6.24; N, 14.30.

Preparation 29

N-(3-Phenoxypropyl)benzeneethanamine hydrochloride [1:1]

A mixture of 30 g (0.14 mole) of 3-phenoxypropyl bromide and 16.82 g (0.139 mole) of phenethylamine in 500 ml of absolute ethanol and in the presence of excess triethylamine was refluxed for 18 hr. The solvent was removed in vacuo and the residue was partitioned between methylene chloride and dilute sodium hydroxide. The methylene chloride solution was dried over magnesium sulfate, and the solvent was removed in vacuo to give an oil. This was dissolved in a mixture of ether and methylene chloride, and the solution was extracted with dilute sulfuric acid and then with dilute sodium hydroxide. The organic solution was treated with an excess of ethereal hydrogen chloride, and 12.43 g (30.68%) of the product precipitated as a white, crystalline solid, mp 196°–197° C.

Analysis: Calculated for $C_{17}H_{22}NOCl$: C, 69.97; H, 7.60; N, 4.80. Found: C, 70.01; H, 7.69; N, 4.82.

Preparation 30

2-(4-Acetylphenoxy)-N-(1-methylethyl)ethanamine

4-Hydroxyphenylmethyl ketone is reacted with 1,2-dibromoethane in the presence of base. The product of that reaction, 2-bromoethyl-4-acetylphenyl ether is then reacted with isopropylamine as in Preparation 26 to give the title compound.

Preparation 31

N-(1-Methylethyl)-2-(4-nitrophenoxy)ethanamine hydrochloride [1:1]

p-Nitrophenol was reacted with 1,2-dibromoethane in the presence of sodium hydroxide to obtain 15.9 g impure 2-bromoethyl-4-nitrophenyl ether. The ether was dissolved in 150 ml of isopropylamine, and the mixture was stirred at room temperature for 21 hr. The solvent was removed in vacuo, and the residue was partitioned between methylene chloride and dilute sodium hydroxide. The methylene chloride was then extracted with several portions of dilute sulfuric acid. The acidic extract was made basic with 50% sodium hydroxide, and the basic solution was extracted with methylene chloride. The methylene chloride extract was dried over magnesium sulfate, and the solvent was removed in vacuo to give an oil, the free base of the title compound. The free base was dissolved in methanol, and the solution was treated with an excess of ethereal hydrogen chloride. White crystalline product, 9.68 g, m.p. 204°–205° C., was obtained.

Analysis: Calculated for $C_{11}H_{17}N_2O_3Cl$: C, 50.68; H, 6.57; N, 10.75. Found: C, 50.70; H, 6.63; N, 10.74.

Preparation 32

Following the procedure of Preparation 23, substituting the following for 2-chloroethyl-p-chlorophenyl sulfone:
(a) 2-chloroethyl 3,5-dichlorophenyl sulfone
(b) 2-chloroethyl 3,4,5-trimethoxyphenyl sulfone,
(c) 2-chloroethyl 4-trifluoromethylphenyl sulfone,
(d) 2-chloroethyl 4-cyanophenyl sulfone,
(e) 2-chloroethyl 4-nitrophenylsulfone,
there are obtained:
(a) N-[2-[(3,5-dichlorophenyl)sulfonyl]ethyl]-1-methylethanamine,
(b) N-[2[(3,4,5-trimethoxyphenyl)sulfonyl]ethyl]-1-methylethanamine,
(c) 1-methyl-N-[2-(4-trifluoromethylphenyl)sulfonyl]ethyl]ethanamine
(d) N-[2-[(4-cyanophenyl)sulfonyl]ethyl-1-methylethanamine, and
(e) 1-methyl-N-[2-[(4-nitrophenyl)sulfonyl]ethyl]ethanamine.

Preparation 33

1-Methyl-N-[2-(1-naphthalenylthio)ethyl]ethanamine hydrochloride [1:1]

To a solution of 143.7 g (0.898 mole) of 1-naphthalenethiol and 50.3 g (0.898 mole) potassium hydroxide in 1 liter of 95% ethanol, which had stirred for 10 minutes at room temperature, was added 1,843.5 g (4.49 moles) of dibromoethane. The resulting solution was heated overnight at gentle reflux, filtered and stripped to dryness. The residue was dissolved in chloroform and extracted with 10% sodium hydroxide. The chloroform layer was evaporated leaving a dark brown oil as residue. The oil was placed in a bomb with 200 ml of isopropylamine and agitated overnight at 100° C. The mixture was evaporated to give an oil which was extracted with water and 10% aqueous sodium hydroxide solution. The chloroform layer was then extracted with 1N sulfuric acid solution. The acidic layer was made alkaline with 50% sodium hydroxide and extracted with chloroform. Evaporation of the chloroform layer gave a dark brown oil, the free base of the title compound.

The oil was reacted with ethereal hydrogen chloride, and the salt was recrystallized from methanol-diethyl ether to give 44.3 g (17.3%) of white crystalline product, m.p. 121°–122.5° C.

Analysis: Calculated for $C_{15}H_{20}NSCl$: C, 63.92; H, 7.15; N, 4.97. Found: C, 63.67; H, 7.17; N, 4.87.

Preparation 34

N-[2-[[4-[2-(Dimethylamino)ethoxy]phenyl]sulfonyl]ethyl]-2-propanamine maleate [1:2]

A mixture of 0.124 mole of sodium hydride (4.96 g of a 60% dispersion in oil; washed with hexane) and 13 g (0.146 mole) of 2-(N,N-dimethylamino)ethanol in 400 ml of dimethyl sulfoxide was stirred at room temperature and under an atmosphere of nitrogen for approximately 0.5 hr. To this solution was added 15.4 g (0.0519 mole) of N-[2-[(4-chlorophenyl)sulfonyl]ethyl]-1-methylethanamine hydrochloride [1:1] (from Preparation 23), and the mixture was stirred at 80°–100° C. for approximately 2 hr. The solvent was removed in vacuo, and the residue was partitioned between methylene chloride and dilute sodium hydroxide. The methylene chloride solution was dried over magnesium sulfate, and the solvent was removed in vacuo to give a liquid. This was treated with approximately 0.1 mole of maleic acid, and the resulting salt was recrystallized from methanol-diethyl ether to give 22.83 g (80.6%) of the product as a white crystalline solid, mp 177.5°–178.5° C.

Analysis: Calculated for $C_{23}H_{34}N_2O_{11}S$: C, 50.54; H, 6.27; N, 5.13. Found: C, 50.53; H, 6.33; N, 5.05.

Preparation 35

2-[4-(Methylthio)phenoxy]ethanol

A mixture of 105.46 g (0.753 mole) of 4-(methylthio)phenol, 62.0 g (0.772 mole) of 2-chloroethanol and 105 g (0.761 mole) of potassium carbonate in approximately one liter of acetonitrile was refluxed overnight. The cooled mixture was filtered, and the solvent was removed in vacuo to give a solid. This was recrystallized from diethyl ether-hexane to give 39.59 g (28.6%) of the product as a white, crystalline solid, mp 55°–56° C.

Analysis: Calculated for $C_9H_{12}O_2S$: C, 58.67; H, 6.56. Found: C, 58.75; H, 6.60.

Preparation 36

2-[4-(Methylsulfonyl)phenoxy]ethanol

A solution of 14.1 g (0.77 mole) of 2-[4-(methylthio)phenoxy]ethanol (from Preparation 35) and 31.2 g (0.18 mole) of m-chlorophenylbenzoic acid in 800 ml of methylene chloride was stirred at room temperature overnight. A saturated, aqueous solution (300 ml) of sodium bisulfite was added, and the mixture was stirred at room temperature for 0.5 hr. The phases were separated, the mthylene chloride solution was dried over magnesium sulfate, and the volume reduced to approximately 100 ml in vacuo. n-Hexane was added until the solution became cloudy, and 9.40 g (56.8%) of the product precipitated as a white, crystalline solid, m.p. 96°–98° C.

Analysis: Calculated for $C_9H_{12}O_4S$: C, 49.99; H, 5.59. Found: C, 49.82; H, 5.58.

Preparation 37

N-[2-[4-(Methylsulfonyl)phenoxy]ethyl]-2-propanamine hydrochloride [1:1]

To a solution 20.5 g (0.095 mole) of 2-[4-(methylsulfonyl)phenoxy]ethanol (from preparation 36) and 12.25 g (0.12 mole) of triethylamine in a mixture of 200 ml of benene and 500 ml of methylene chloride was slowly added a solution of 14.31 g (0.125 mole) of mesyl chloride in methylene chloride, and the solution was stirred at room temperature for 2 hours. The solvent was removed in vacuo, and the residue was partitioned between methylene chloride and dilute sodium hydroxide. The methylene chloride solution was dried over magnesium sulfate, the solvent was removed in vacuo, and the residue was partitioned between methylene chloride and dilute sodium hydroxide. The methylene chloride phase was extracted with dilute sulfuric acid. The acidic extract was made basic with 50% sodium hydroxide, and the basic solution was extracted with methylene chloride. The methylene chloride solution was dried over magnesum sulfate and the solvent was removed in vacuo to give 17.45 g (62.7%) of the free base of the product as a solid. Part of this was converted to the hydrochloride salt, and the salt was recrystallized from mthanol/diethyl ether to give the product as a white, crystalline solid, m.p. 182°–184° C.

Analysis: Calculated for $C_{12}H_{20}NO_3SCl$: C, 49.06; H, 6.80; N, 4.77. Found: C, 49.00; H, 6.92; N, 4.76.

Preparation 38

N-[2-[4-(Methylthio)phenoxy]ethyl]-2-propanamine hydrochloride [1:1]

A solution of 22.2 g (0.121 mole) of 2-[4-(methylthio)phenoxy]ethanol (from preparation 35), 16.41 g (0.143 mole) of mesyl chloride and an excess of triethylamine in 800 ml of benzene was stirred at room temperature for 2 hours. The mixture was extracted with water and then with dilute sodium hydroxide. The benzene solution was dried over magnesium sulfate, and the solvent was removed in vacuo. The residue was dissolved in 300 ml of isopropylamine, and the mixture was stirred at room temperature overnight. The solvent was removed in vacuo, and the residue was dissolved in methylene chloride. The methylene chloride solution was extracted with dilute sodium hydroxide and then with dilute sulfuric acid. The acidic extract was made basic with 50% sodium hydroxide, and the basic solution was extracted with methylene chloride. The methylene chloride solution was dried over magnesium sulfate, and the solvent was removed in vacuo to give the free base of the product as an oil. The free base was convreted to the hydrochloride salt, and the salt was recrystallized from methanol-diethyl ether to give 23.9 g (76%) of the product as a white, crystalline solid, m.p. 183.5°–185° C.

Analysis: Calculated for $C_{12}H_{20}NOSCl$: C, 55.05; H, 7.70; N, 5.35. Found: C, 54.99; H, 7.72; N, 5.34.

Preparation 39

N-[2-[4-(Methylsulfinyl)phenoxy]ethyl]-2-propanamine oxalate [1:1]

A solution of 10.11 g (0.0386 mole) of N-[2-[4-(methylthio)phenoxy]ethyl]-2-propanamine hydrochloride [1:1](from Preparation 38) and 8.46 g (0.055 mole) of sodium perborate in 500 ml of 2M sulfuric acid was stirred at room temperature for 19 hours. The reaction mixture was poured over ice and was made basic with 50% sodium hydroxide. The basic mixture was extracted with methylene chloride, the methylene chloride solution was dried over magnesium sulfate and the solvent was removed in vacuo to give the free base of the product as an oil. The free base was converted to the hydrochloride salt, and the salt was recrystallized from methanol-diethyl ether to give 11.66 g (91.2%) of the product as a white, crystalline solid, m.p. 137°–139° C.

Analysis: Calculated for $C_{14}H_{21}NO_6S$: C, 50.74; H, 6.39; N, 4.23. Found: C, 50.63; H, 6.40; N, 4.19.

Preparation 40

N-[4-(3-Chloropropoxy)phenyl]acetamide

A mixture of 4-acetamidophenol (182.2 g, 1.2 moles), bromochloropropane (157.4 g, 1.0 mole), and potassium carbonate (145.0 g, 1.05 moles) was refluxed overnight in 700 ml of acetone. The acetone solution formed white crystals after being placed in a refrigerator overnight. The solution was filtered and the crystals washed with acetone. The filtrate was stripped to dryness, and the residue dissolved in chloroform and extracted with a 5% sodium hydroxide solution. Removal of the chloroform gave an oil. The white crystals obtained earlier were also dissolved in chloroform and extracted with a 5% sodium hydroxide solution. Removal of the chloroform gave a white solid. The white solid and oil were combined with acetone and placed in a refrigerator; white crystals were obtained. A 5-g sample of the white solid was recrystallized from acetone a second time to furnish 1.76 g (after drying in vacuo overnight at 80° C.) (23% yield) of white crystalline product, m.p. 125°–127° C.

Analysis: Calculated for $C_{11}H_{14}NO_2Cl$: C, 58.03; H, 6.20; N, 6.15. Found: C, 58.21; H, 6.28; N, 6.15.

Preparation 41

1-[4-(4-Bromobutoxy)-3-methoxyphenyl]ethanone.

To a warm solution of 12.7 g (0.55 mole) of sodum metal in 500 ml of absolute ethanol was added a slurry of 83.1 g (0.5 mole) of acetovanillone in 250 ml of absolute ethanol. All solids dissolved and then a solid precipitated. The mixture was stirred at ambient temperature for 1 hr and then added over a 3 hr preiod to a solution at reflux of 177 g (0.82 mole) of 1,4-dibromobutane in 500 ml of absolute ethanol. After addition was complete, the mixture was heated at reflux overnight. The mixture was concentrated under reduced pressure, and the residue was partitioned between 1.5 liter of benzene and 1 liter of water. The mixture was filtered to remove an insoluble material. The filtrate layers were separated, and the organic layer was washed with four 300 ml portions of a 5% sodium hydroxide solution, once with water and once with brine, dried over sodium sulfate and concentrated under reduced pressure to give 138 g of gummy solid as residue. This solid was purified by column chromatography on 1 kg of silica gel and eluted wth 2% ethyl acetate in benzene to yield 69.6 (46%) of the title compound as an off-white solid, m.p. 52°–54° C. (isopropyl ether).

Analysis: Calculated for $C_{13}H_{17}BrO_3$: C, 51.84; H, 5.69. Found: C, 52.03; H, 5.76.

Preparation 42

4-(3-Chloropropoxy)benzamide

A mixture of 50 g (0.365 mole) of 4-hydroxybenzamide, 114.8 g (0.729 mole) of 1-bromo-3-chloropropane and 151.3 g (1.1 mole) of anhydrous potassium carbonate in 1 liter of acetone was heated at reflux for 20 hr. The mixture was concentrated under reduced pressure and the rsidue was stirred with 1.2 liter of water to remove inorganic solids. The mixture was filtered and the filter cake was washed with water and petroleum ether and dried to yield 75.5 g (97%) of the title compound as a white solid. An analytical sample was recrystallized from ethyl acetate, m.p. 142°–143° C.

Analysis: Calculated for $C_{10}H_{12}ClNO_2$: C, 56.22; H, 5.66; N, 6.56. Found: C, 55.92; H, 5.61; N, 6.56.

Preparation 43

Following the procedure of Preparation 2 and substituting the following for [(2-chloroethyl)sulfonyl]benzene:

(a) N-[4-(3-chloropropoxy)phenyl]acetamide (obtained in Preparation 40),
(b) 1-[4-(4-bromobutoxy)-3-methoxyphenyl]ethanone (obtained in Preparation 41), and
(c) 4-(3-chloropropoxy)benzamide (obtained in Preparation 42), there are obtained:
(a) N-[4-[3-[[2-(diethylamino)ethyl]amino]propoxy]phenyl]acetamide,
(b) 1-[4-[3-[[2-(diethylamino)ethyl]amino]propyl]-3-methoxyphenoxy]ethanone, and
(c) 4-[4-[[2-(diethylamino)ethyl]amino]butoxy]benzamide.

Preparation 44

In methanol solvent and dehydrogenating over a nickel/copper/chromium catalyst as in the method of Yeakey, et al., in Ger. Offen. 3,048,832 from the following compounds:
(a) 2-(dimethylamino)ethanamine,
(b) 2-(diethylamino)ethanamine,
(c) 2-(dipropylamino)ethanamine,
(d) 3-(dimethylamino)propanamine,
(e) 3-(diethylamino)propanamine,
(f) 3-(dipropylamino)propanamine,
(g) 2-(4-morpholinyl)ethanamine,
(h) 3-(4-morpholinyl)propanamine,
(i) 2-[1-[(4-phenyl)piperazinyl]]ethanamine,
(j) 3-[1-[(4-phenyl)piperazinyl]]propanamine,
(k) 2-[1-(4-methyl)piperazinyl]ethanamine,
(l) 3-[1-(4-methyl)piperazinyl]propanamine,
(m) 2-(1-pyrrolidinyl)ethanamine, and
(n) 3-(1-pyrrolidinyl)propanamine, there are obtained
(a) N'-[2-(dimethylamino)ethyl]-N,N-dimethyl-1,2-ethanediamine,
(b) N-'[2-(diethylamino)ethyl]-N,N-diethyl-1,2-ethanediamine,
(c) N'-[2-(dipropylamino)ethyl]-N,N-dipropyl-1,2-ethanediamine,
(d) N'-[3-(dimethylamino)propyl]-N,N-dimethyl-1,3-propanediamine,
(e) N'-[3-(diethylamino)propyl]-N,N-diethyl-1,3-propanediamine,
(f) N'-[3-(dipropylamino)propyl]-N,N-dipropyl-1,3-propanediamine,
(g) 2-(4-morpholinyl)-N-[2-(4-morpholinyl)ethyl]ethanamine,
(h) 3-(4-morpholinyl)-N-[3-(4-morpholinyl)propyl]-1-propanamine,
(i) 2-[1-(4-phenyl)piperazinyl]-N-[2-[1-(4-phenyl)piperazinyl]ethyl]ethanamine,
(j) 3-[1-(4-phenyl)piperazinyl]-N-[3-[1-(4-phenyl)piperazinyl]propyl]-1-propanamine,
(k) 2-[1-(4-methyl)piperazinyl]-N-[2-[1-(4-methyl)piperazinyl]ethyl]ethanamine,
(l) 3-[1-(4-methyl)piperazinyl]-N-[3-[1-(4-methyl)piperazinyl]propyl]propanamine, (m) 2-(1-pyrrolidinyl)-N-[2-(1-pyrrolidinyl)ethyl]ethanamine, and
(n) 3-(1-pyrrolidinyl)-N-[3-(1-pyrrolidinyl)propyl]-1-propanamine.

Preparation 45

N'-Cyano-N-[3-(diethylamino)propyl]-N-[2-(phenylsulfonyl)ethyl]carbamimidothioic acid methyl ester oxalate [1:1]

A mixture of 17.88 g (0.060 mole) of N,N-diethyl-N'-[2-(phenylsulfonyl)ethyl]-1,3-propanediamine (oil obtained in Preparation 1), and 12.78 g (0.088 mole) of dimethyl N-cyanodithioiminocarbonate in 500 ml of absolute ethanol was stirred at room temperature for 16 hr, and then was refluxed for 3 hr. The solvent was removed in vacuo, and the residue was dissolved in diethyl ether. This solution was treated with a solution of oxalic acid in methanol to give a white precipitate. This was recrystallized from methanol-ether to give 18.13 g (62.1%) of the title compound as a white crystalline solid, m.p. 105°–107° C.

Analysis: Calculated for $C_{20}H_{30}N_4O_6S$: C, 49.37; H, 6.21; N, 11.51. Found: C, 49.03; H, 6.32; N, 11.40.

Preparation 46

Following the procedure of Preparation 45 and substituting the following for N,N-diethyl-N'-[2-(phenylsulfonyl)ethyl]-1,3-propanediamine:
(a) N,N-diethyl-N'-[2-(phenylsulfinyl)ethyl]-1,2-ethanediamine (oil obtained in Preparation 12),
(b) N,N-diethyl-N'-(3-phenylpropyl)-1,2-ethanediamine (oil obtained in Preparation 11),
(c) N,N-diethyl-N'-[2-(phenylthio)ethyl]-1,2-ethanediamine (oil obtained in Preparation 10), and
(d) N,N-diethyl-N'-(2-phenoxyethyl)-1,2-ethanediamine (free base obtained in Preparation 9), there are obtained :
(a) N'-cyano-N-[2-(diethylamino)ethyl]-N-[2-(phenylsulfinyl)ethyl]carbamimidothioic acid methyl ester oxalate,
(b) N'-cyano-N-[2-(dimethylamino)ethyl]-N-(3-phenylpropyl)carbamimidothioic acid methyl ester oxalate,
(c) N'-cyano-N-[2-(diethylamino)ethyl]-N-[2-(phenylthio)ethyl]carbamimidothioic acid methyl ester oxalate, and
(d) N'-cyano-N-[2-(diethylamino)ethyl]-N-(2-phenoxyethyl)carbamimidothioic acid methyl ester oxalate.

Preparation 47

Following the procedure of Preparation 29 and substituting the following for phenethylamine:
(a) 4-aminotoluene,
(b) 3-bromoaniline,
(c) 2,4,6-tribomoaniline,
(d) 4-methoxyaniline,
(e) 4-nitroaniline,
(f) 4-aminobenzotrifloride and
(g) 4-aminobenzonitrile there are obtained:
(a) 4-methyl-N-(3-phenoxypropyl)benzeneamine,
(b) 3-bromo-N-(3-phenoxypropyl)benzeneamine,
(c) 2,4,6-tribromo-N-(3-phenoxypropyl)benzeneamine,
(d) 4-methoxy-N-(3-phenoxypropyl)benzeneamine,
(e) 4-nitro-N-(3-phenoxypropyl)benzeneamine,
(f) N-(3-phenoxypropyl)-3-(trifluoromethyl)benzeneamine, and
(g) 4-[(3-phenoxypropyl)amino]benzonitrile.

Preparation 48

2-(Phenylsulfonyl)ethanamine hydrochloride [1:1].

A solution of 32.3 g (0.102 mole) of 2-[2-(phenylsulfonyl)ethyl]-1H-isoindole-1,3-(2H)-dione and 11.8 g (0.2 mole) of 85% hydrazine hydrate in 500 ml of absolute ethanol was refluxed for 6 hr. The reaction mixture was cooled to room temperature, filtered and concentrated. The concentrate was dissolved in chloroform and extracted with a 5% sodium hydroxide solution. The chloroform layer was dried and evaporated to give a clear oil. The oil (the free base of the title compound) was reacted with ethereal hydrogen chloride. Recrystallization of the precipitated salt from methanol-diethyl ether gave white crystalline product (40.5% yield), m.p. 151°–154° C.

Analysis: Calculated for $C_8H_{12}NO_2SCl$: C, 43.34; H, 5.46; N, 6.32. Found: C, 43.09; H, 5.44; N, 6.42.

Preparation 49

(1-Methylethyl)[2-(phenylsulfonyl)ethyl]carbamic chloride.

A solution of phosgene in benzene (60 ml, 1.9M, 12.5% in benzene) in 350 ml of methylene chloride was prepared. To this solution was added a methylene chloride solution of 1-methyl-N-[2-(phenylsulfonyl ethyl]ethanamine (free base of Preparation 21, 1013 g, 0.045 mole) and 1,8-bis(dimethylamino)naphthyl (9.55 g, 0.045 mole) over 0.5 hour. The resulting solution was stirred 2 hours at room temperature and extracted with 1N sulfuric acid. The methylene chloride solution was dried over anhydrous potassium carbonate, filtered, and solvent removed to give a blue oil. The oil was triturated with diethyl ether, and a white solid crystallized in about two minutes. The solid was dried overnight in vacuo at 80° C.; this produced 9.57 g (73.4% yield) of white crystalline solid, m.p. 79°–81° C.

Analysis: Calculated for $C_{12}H_{16}NO_3SCl$: C, 49.74; H, 5.56; N, 4.83. Found: C, 49.89; H, 5.62; N, 4.86.

Preparation 50

N'-[2-(Diethylamino)ethyl]-N,N-diethyl-1,2-ethanediamine maleate [1:3].

A mixture of 69.16 g (0.402 mole) of N-(2-chloroethyl)-N,N-diethylamine hydrochloride and 300 ml of N,N-diethylethylenediamine was stirred at room temperature for 40 hr. Solid potassium carbonate (150 g) was added, and the mixture was stirred for several hours. The mixture was filtered and the filtrate was distilled under high vacuum. The portion boiling at 73°–75° C. (0.6 mmHg) was collected to give 34.9 g (40.4%) of the non-salt form of the title compound as a liquid. A portion of this was converted to the maleate salt, and the salt was recrystallized from methanol-ether to give the title compound as a white, crystalline solid, m.p. 183°–184.5° C. Analysis: Calculated for $C_{24}H_{41}N_3O_{12}$: C, 51.15; H, 7.33; N, 7.46. Found: C, 51.11; H, 7.40; N, 7.43.

EXAMPLE 1

N'-[2-(Diethylamino)ethyl]-N-[3-(diethylamino)propyl]-N-[2-(phenylsulfonyl)ethyl]urea oxalate [1:2].

A mixture of 4.59 g (0.0283 mole) of 1,1'-carbonyldiimidazole and 3.018 g (0.0260 mole) of diethylaminoethylamine in 200 ml of tetrahydrofuran was stirred at 25° C. for 1 hr. A solution of 6.71 g (0.0225 mole) of N,N-diethyl-N'-[2-(phenylsulfonyl)ethyl]-1,3-propanediamine in 200 ml of tetrahydrofuran was added, and the solution was refluxed for 16 hr. The solvent was removed in vacuo and the residue was partitioned between methylene chloride and water. The methylene chloride solution was dried over magnesium sulfate and the solvent was removed in vacuo to give the free base of the title compound as an oil. This was converted to the dioxalate salt, and the salt was recrystallized from methanol-ether to give 9.95 g (71.3%) of the title compound as a white crystalline solid, m.p. 119°–120° C. with decomposition.

Analysis: Calculated for $C_{26}H_{44}N_4O_{11}S$: C, 50.31; H, 7.15; N, 9.03. Found: C, 50.05; H, 7.18; N, 8.94.

EXAMPLE 2

N,N'-Bis[2-(diethylamino)ethyl]-N-[2-(phenylsulfonyl)ethyl]urea oxalate [1:2]

A solution of 5.59 g (0.0345 mole) of 1,1'-carbonyldiimidazole and 3.71 g (0.032 mole) of diethylaminoethylamine in 400 ml of tetrahydrofuran was stirred for 50 minutes at room temperature. A solution of 7.92 g (0.0279 mole) of N,N-diethyl-N'-[2-(phenylsulfonyl)ethyl]-1,2-ethanediamine in 100 ml of tetrahydrofuran was added, and the mixture was refluxed for 16 hours. The solvent was removed in vacuo, and the residue was partitioned between methylene chloride and water. The methylene chloride solution was dried over sodium sulfate, and the solvent was removed in vacuo to give the free base of the title compound. This was converted to the dioxalate salt, and the salt was recrystllized from methanol-ether to give 13.03 g (62.3% of the title compound, a white crystalline solid, m.p. 95°–97° C.

Analysis: Calculated for $C_{25}H_{42}N_4O_{11}S$: C, 49.49; H, 6.98; N, 9.24. Found: C, 49.16; H, 6.98; N, 9.36.

EXAMPLE 3

N'-[2-(Diethylamino)ethyl]-N-[2-(4-morpholinyl)ethyl]-N-[2-(phenylsulfonyl)ethyl]urea oxalate hydrate [1:2:1]

A mixture of 4.70 g (0.029 mole) of 1,1'-carboyldiimidazole and 3.14 g (0.027 mole) of N,N-diethylethylenediamine in 40 ml of tetrahydrofuran was stirred at room temperature for 1 hr. A solution of 7.28 g (0.0244 mole) of N-[2-(phenylsulfonyl)ethyl]-4-morpholineethanamine in 50 ml of tetrahydrofuran was added, and the mixture was refluxed for 16 hr. The solvent was removed in vacuo, and the residue was partitioned between methylene chloride and water. The methylene chloride phase was dried over magnesium sulfate, and the solvent was removed in vacuo to give an oil. The oil was dissolved in methanol, 2 equivalents of oxalic acid were added, and diethyl ether was added. A white solid precipitated to give 10.33 g (66.3%) of the title compound, a white crystalline solid, m.p. 98°–100° C.

Analysis: Calculated for $C_{25}H_{42}N_4O_{13}S$: C, 47.01; H, 6.63; N, 8.77. Found: C, 46.87; H, 6.47; N, 8.83.

EXAMPLE 4

N'-2-(Diethylamino)ethyl]-N-[2-(phenylsulfonyl)ethyl]-N-[2-(1-pyrrolidinyl)ethyl]urea oxalate hydrate [1:2:0.5]

A mixture of 4.22 g (0.026 mole) of 1,1'-carbonyldiimidazole and 2.78 g (0.024 mole) of N,N-diethylethylenediamine in 400 ml of tetrahydrofuran was stirred at room temperature for 1 hr. A solution of 5.60 g (0.0199 mole) of N-[2-(phenylsulfonyl)ethyl]-1-pyrrolidineethanamine in 50 ml of tetrahydrofuran was added and the mixture was refluxed for 24 hr. The solvent was removed in vacuo, and the residue was partitioned between methylene chloride and water. The methylene chloride solution was dried over magnesium sulfate, and the solvent was removed in vacuo to give an oil. This oil was dissolved in methanol, two equivalents of oxalic acid were added, and diethyl ether was added. A white pecipitate formed to give 7.67 g of impure product. This was recrystllized from methanol-diethyl ether to give 2.94 g (24.01%) of the title compound, a white crystalline solid; m.p. 132°–133.5° C.

Analysis: Calculated for $C_{25}H_{41}N_4O_{11.5}S$: C, 48.93; H, 6.73; N, 9.13. Found: C, 48.82; H, 6.64; N, 9.29.

An additional 3.31 g (27.1%) of title compound was isolated from the filtrate as a white crystalline solid, m.p. 132°–133° C.

EXAMPLE 5

N-[2-(Diethylamino)ethyl]-N'-[2-(methylphenylamino)ethyl]-N-[2-(phenylsulfonyl)ethyl]urea fumarate [1:1]

A mixture of 4.21 g (0.026 mole) of 1,1'-carbonyldiimidazole and 3.60 g (0.024 mole) of N-(2-aminoethyl)-N-methylaniline in 400 ml of tetrahydrofuran was stirred at room temperature for 1 hr. A solution of 6.56 g (0.0231 mole) of N,N-diethyl-N'-[2-(phenylsulfonyl)ethyl]-1,2-ethanediamine in 50 ml of tetrahydrofuran was added, and the mixture was refluxed for 16 hr. The solvent was removed in vacuo, and the residue partitioned between methylene chloride and dilute sodium hydroxide solution. The methylene chloride solution was dried over magnesium sulfate, and the solvent was removed in vacuo to give the free base of the title compound, an oil. This was dissolved in a mixture of methanol and ether, a solution of fumaric acid in methanol was added and diethyl ether was added. A white prcipitate was collected to give 8.51 g (63.9%) of the title compound, a white crystalline solid, m.p. 133°–135° C.

Analysis: Calculated for $C_{28}H_{40}N_4O_7S$: C, 58.32; H, 6.99; N, 9.72. Found: C, 58.35; H, 7.03; N, 9.65.

EXAMPLE 6

N'-[2-(Diethylamino)ethyl]-N-[2-(-1-homopiperidinyl)ethyl]-N-[2-(phenylsulfonyl)ethyl]urea oxalate hydrate [1:2:0.5]

A mixture of 3.89 g (0.024 mole) of 1,1'-carbonyldiimidazole and 2.67 g (0.023 mole) of N,N-diethylethylenediamine in 400 ml of tetrahydrofuran was stirred at room temperature for 1 hr. A solution of 5.95 g (0.0192 mole of N-[2-(phenylsulfonyl)ethyl]-homopiperidineethanamine in 50 ml of tetrahydrofuran was added, and the mixture was refluxed for 16 hr. The solvent was removed in vacuo, and the residue was partitioned between methylene chloride and water. The volume of the methylene chloride solution was reduced to ~400 ml in vacuo and 300 ml of diethyl ether was added. The organic solution was extracted with three portions of water and was dried over magnesium sulfate. The solvent was removed in vacuo to give the free base of the title compound, an oil.

The free base was converted to the oxalate salt, and the salt was recrystallized from methanol/diethyl ether to give 8.86 g (72.9%) of the title compound, a white crystalline solid, m.p. 95°–98° C.

Analysis: Calculated for $C_{27}H_{45}N_4O_{11.5}S$: C, 50.53; H, 7.07; N, 8.73. Found: C, 50.47; H, 6.91; N, 8.77.

EXAMPLE 7

N-[2-(Diethylamino)ethyl]-N'-[3-(diethylamino)-propyl]-N-[2-(phenylsulfonyl)ethyl]urea oxalate hydrate [1:2:0.5]

A mixture of 3.00 g (0.023 mole) of 3-diethylaminopropylamine and 3.90 g (0.0241 mole) of 1,1'-carbonyldiimidazole in 400 ml of tetrahydrofuran was stirred at room temperature for 1 hr. A solution of 5.54 g (0.0195 mole) of N,N-diethyl-N'-[2-(phenylsulfonyl)ethyl]-1,2-ethanediamine in 50 ml of tetrahydrofuran was added, and the mixture was refuxed for 24 hr. The solvent was removed in vacuo, and the residue was dissolved in a mixture of 300 ml of methylene chloride and 500 ml of diethyl ether. The solution was extracted with water and was dried over magnesium sulfate. The solvent was removed in vacuo to give an oil. This was converted to the dioxalate salt, and the salt was recrystllized from methanol-diethyl ether to give 7.57 g (61.6%) of the title compound, a solid, m.p. 57°–62° C.

Analysis: Calculated for $C_{26}H_{45}N_4O_{11.5}S$: C, 49.59; H, 7.20; N, 8.90. Found: C, 49.49; H, 7.17; N, 8.84.

EXAMPLE 8

N'-[2-(Diethylamino)ethyl]-N-[2-(methylphenylamino)ethyl]-N-[2-(phenylsulfonyl)ethyl]urea oxalate [1:1:0.5]

A mixture of 4.70 g (0.029 mole) of 1,1'-carbonyldiimidazole and 3.13 g (0.027 mole) of N,N-diethylethylenediamine in 400 ml of tetrahydrofuran was stirred at room temperature for 1 hr. A solution of 5.85 g (0.0184 mole) of N-methyl-N-phenyl-N'-[2-(phenylsulfonyl)ethyl]-1,2-ethanediamine in 50 ml of tetrahydrofuran was added, and the solution was refluxed for 16 hr. The solvent was removed in vacuo, and the residue was partitioned between diethyl ether and water. The diethyl ether solution was dried over magnesium sulfate, and the solvent was removed in vacuo to give the free base of the title compound, an oil. This was converted to the oxalate salt, and the salt was recrystallized from methanol-diethyl ether to give 8.64 g (85.9%) of the title compound, a white crystalline solid, m.p. 154.5°–155.5° C.

Analysis: Calculated for $C_{26}H_{39}N_4O_{7.5}S$: C, 55.80; H, 7.02; N, 10.01. Found: C, 56.13; H, 6.93; N, 10.12.

EXAMPLE 9

N'-[2-(Diethylamino)ethyl]-N-[2-(phenylsulfonyl)ethyl]-N-[2-(1-piperidinyl)ethyl]urea oxalate hydrate [1:2:1]

A mixture of 3.89 g (0.024 mole) of 1,1'-carbonyldiimidazole and 2.55 g (0.022 mole) of N,N-diethylethylenediamine in 400 ml of tetrahydrofuran was stirred for 1 hr at room temperature. A solution of 5.65 g (0.0191 mole) of N-[2-(phenylsulfonyl)ethyl]-1-piperidineethanamine in 50 ml of tetrahydrofuran was added, and the solution was refluxed for 16 hr. The solvent was removed in vacuo, and the residue was partitioned between methylene chloride and water. The methylene chloride solution was dried over magnesium sulfate, and the solvent was removed in vacuo to give the free base of the title compound, an oil. This was converted to the dioxalate salt, and the salt was recrystallized from methanol-diethyl ether to give 9.37 g of the title compound. This was recrystallized once again to give 7.71 g (63.4%) of the title compound, a white crystalline solid, m.p. 112°–115° C.

Analysis: Calculated for $C_{26}H_{44}N_4O_{12}S$: C, 49.05; H, 6.97; N, 8.80. Found: C, 48.65; H, 6.93; N, 8.94.

EXAMPLE 10

N'-[2-(Diethylamino)ethyl]-N-[2-(dimethylamino)ethyl]-N-[2-(phenylsulfonyl)ethyl]urea oxalate hydrate [1:2:0.5]

A mixture of 2.78 g (0.024 mole) of N,N-diethylethylenediamine and 4.22 g (0.026 mole) of 1,1'-carbonyldiimidazole in 400 of tetrahydrofuran was stirred at room temperature for 1 hr. A solution of 5.20 g (0.0203 mole) of N,N-dimethyl-N'-[2-(phenylsulfonyl)ethyl]-1,2-ethanediamine in 50 ml of tetrahydrofuran was added, and the solution was refluxed for 20 hr. The solvent was removed in vacuo, and the residue was partitioned between methylene chloride and water. The methylene chloride solution was dried over magnesium sulfate, and the solvent was removed in vacuo to give the free base of the title compound, an oil. This was converted to the oxalate salt, and the salt was recrystallized from methanol-diethyl ether to give 8.39 g (70.3%) of the title compound, a white crystalline salt, m.p. 116°–118° C.

Analysis: Calculated for $C_{23}H_{39}N_4O_{11.5}S$: C, 47.01; H, 6.69; N, 9.53. Found: C, 47.27; H, 6.64; N, 9.74.

EXAMPLE 11

N-[2-(Diethylamino)ethyl]-N-[2-(phenylsulfonyl)ethyl]-N'-[2-(1-piperidinyl)ethyl]urea citrate [1:2]

A mixture of 3.89 g (0.024 mole) of 1,1'-carbonyldiimidazole and N-(2-aminoethyl)piperidine in 400 ml of tetrahydrofuran was stirred at room temperature for 1 hr. A solution of 5.58 g (0.0197 mole) of N,N-diethyl-N'-[2-(phenylsulfonyl)ethyl]-1,2-ethanediamine in 50 ml of tetrahydrofuran was added, and the solution was refluxed for 16 hr. The solvent was removed in vacuo, and the residue was partitioned between a mixture of diethyl ether-methylene chloride (60/40) and water. The organic phase was dried over magnesium sulfate, and the solvent was removed in vacuo to give the free base of the title compound, an oil. This was converted to the dicitrate salt, and the salt was recrystallized from methanol-diethyl ether to give 6.93 g (42.78%) of title compound, a white crystalline solid, m.p. 86°–90° C.

Analysis: Calculated for $C_{34}H_{54}N_4O_{17}S$: C, 49.63; H, 6.62; N, 6.81. Found: C, 49.34; H, 6.70; N, 6.70.

EXAMPLE 12

N-[2-(Diethylamino)ethyl]-N'-[3-(diethylamino)-propyl]-N-[2-(phenylsulfonyl)ethyl]thiourea oxalate [1:2]

A mixture of 5.51 g (0.0194 mole) of N,N-diethyl-N'-[2-(phenylsulfonyl)ethyl]-1,2-ethanediamine and 3.50 g (0.0203 mole) of 3-(diethylamino)propylisothiocyanate in 500 ml of acetonitrile was refluxed for 16 hours. The solvent was removed in vacuo, and the residue was partitioned between methylene chloride and water. The methylene chloride solution was dried over magnesium sulfate, and the solvent was removed in vacuo to give an oil. This was converted to the dioxalate salt, and the salt was recrystallized from methanol-diethyl ether to give 10.2 g (83.3%) of the title compound, a white crystalline solid, m.p. 105°–107° C. with decomposition.

Analysis: Calculated for $C_{26}H_{44}N_4O_{10}S_2$: C, 49.04; H, 6.97; N, 8.80. Found: C, 48.72; H, 6.94; N, 8.73.

EXAMPLE 13

N,N'-Bis[2-(diethylamino)ethyl]-N-(2-phenoxyethyl)urea citrate [1:2]

A mixture of 2.72 g (0.0235 mole) of N,N-diethylethylenediamine and 4.37 g (0.027 mole) of 1,1'-carbonyldiimidazole in 400 ml of tetrahydrofuran was stirred at room temperature for 1 hr. A solution of 5.11 g (0.0216 mole) of N,N-diethyl-N'-(2-phenoxyethyl)-1,2-ethanediamine in 50 ml of tetrahydrofuran was added, and the solution was refluxed for 20 hr. The solvent was removed in vacuo and the residue was dissolved in a mixture of 250 ml of diethyl ether and 250 ml of methylene chloride. The solution was extracted with several portions of water and was dried over magnesium sulfate. The solvent was removed in vacuo to give an oil. A solution of the oil in methanol was treated with a two-fold excess of citric acid, diethyl ether was added, and 12.22 g (74.2%) of the title compound crystallized as a white crystalline solid, m.p. 80°–85° C.

Analysis: Calculated for $C_{33}H_{54}N_4O_{16}$: C, 51.96; H, 7.14; N, 7.35. Found: C, 51.71; H, 7.16; N, 7.28.

EXAMPLE 14

N,N'-Bis[2-(diethylamino)ethyl]-N-[2-(phenylthio)ethyl]urea citrate [1:2]

A solution of 8.75 g (0.054 mole) of 1,1'-carbonyldiimidazole and 5.68 g (0.049 mole) of N,N-diethylethylenediamine in 400 ml of tetrahydrofuran was stirred at room temperature for 1 hr. A solution of 11.44 g (0.0454 mole) of N,N-diethyl-N'-[2-(phenylthio)ethyl]-1,2-ethanediamine in 100 ml of tetrahydrofuran was added, and the solution was refluxed for 16 hr. The solvent was removed in vacuo, and the residue was partitioned between methylene chloride and water. The methylene chloride solution was dried over magnesium sulfate, and the solvent was removed in vacuo to give the free base of the title compound, an oil. This was converted to the dicitrate salt, and the salt was recrystallized from methanol-diethyl ether to give 29.75 g (84.98%) of title compound, a white crystalline salt, m.p. 106°–109° C.

Analysis: Calculated for $C_{33}H_{54}N_4O_{15}S$: C, 50.89; H, 6.99; N, 7.19. Found: C, 50.62; H, 7.09; N, 7.22.

EXAMPLE 15

N,N'-Bis[2-(diethylamino)ethyl]-N-(3-phenylpropyl)urea citrate hydrate [1:2:0.5]

A solution of 8.70 g (0.053 mole) of 1,1'-carbonyldiimidazole and 5.59 g (0.048 mole) of N,N-diethylethylenediamine in 400 ml of tetrahydrofuran was stirred at room temperature. A solution of 11.00 g (0.047 mole) of N,N-diethyl-N'-(3-phenylpropyl)-1,2-ethanediamine was added, and the solution was refluxed for 16 hr. The solvent was removed in vacuo, and the residue was partitioned between methylene chloride and water. The methylene chloride solution was dried over magnesium sulfate, and the solvent was removed in vacuo to give the free base of the title compound, an oil.

This was converted to the dicitrate salt, and the salt was recrystallized from methanol-diethyl ether to give 29.88 g (80.4%) of the title compound, a white crystalline solid, m.p. 93°–95° C.

Analysis: Calculated for $C_{34}H_{57}N_4O_{15.5}$: C, 53.05; H, 7.46; N, 7.28. Found: C, 52.94; H, 7.43; N, 7.34.

EXAMPLE 16

N,N'-Bis[2-(diethylamino)ethyl]-N-[2-(phenylsulfonyl)ethyl]urea citrate hydrate [1:2:0.5]

A solution of 5.35 g (0.033 mole) of 1,1'-carbonyldiimidazole and 3.53 g (0.030 mole) of diethylethylenediamine in 400 ml of tetrahydrofuran was stirred at room temperature for 1 hr. A solution of 6.48 g (0.028 mole) of N,N-diethyl-N'-[2-(phenylsulfinyl)ethyl]-1,2-ethanediamine in 100 ml of tetrahydrofuran was added, and the solution was refluxed for 16 hr. The solvent was removed in vacuo, and the residue was partitioned between methylene chloride and water. The methylene chloride solution was dried over magnesium sulfate, and the solvent was removed in vacuo to give the free base of the title compound, an oil. This was converted to the dicitrate salt, and the salt was recrystallized from methanol-diethyl ether to give 16.21 g (72.0%) of the title compound as a glossy white solid, m.p. 70°–75° C.

Analysis: Calculated for $C_{33}H_{55}N_4O_{16.5}S$: C, 49.31; H, 6.90; N, 6.97. Found: C, 49.39; H, 7.12; N, 7.05.

EXAMPLE 17

N,N'-Bis[2-(diethylamino)propyl]-N-[2-(phenylsulfonyl)ethyl]urea citrate hydrate [1:2:0.5]

A mixture of 8.42 g (0.052 mole) of 1,1'-carbonyldiimidazole and N,N-diethyl-1,3-propanediamine in 400 ml of tetrahydrofuran was stirred at room temperature for 1 hr. A solution of 12.5 g (0.042 mole) of N,N-diethyl-N'[2-(phenylsulfonyl)ethyl]-1,3-propanediamine in 50 ml of tetrahydrofuran was added, and the mixture was refluxed for 16 hr. The solvent was removed in vacuo, and the residue was partitioned between methylene chloride and water. The methylene chloride solution was dried over sodium sulfate. The solvent was removed in vacuo to give the free base of the title compound, an oil. This was converted to the dicitrate salt, and the salt was recrystallized from methanol-diethyl ether to give 23.63 g (66.4%) of the title compound, a white crystalline solid, m.p. 88°–92° C.

Analysis: Calculated for $C_{35}H_{59}N_4O_{17.5}S$: C, 49.58; H, 7.01; N, 6.61. Found: C, 49.48; H, 7.04; N, 6.60.

EXAMPLE 18

N-[4-(Diethylamino)butyl]-N'-[2-(diethylamino)ethyl]-N-[2-(phenylsulfonyl)ethyl]urea citrate hydrate [1:2:0.5]

A mixture of 5.90 g (0.036 mole) of 1,1'-carbonyldiimidazole and 3.48 g (0.030 mole) of N,N-diethylethylenediamine in 400 ml of tetrahydrofuran was stirred at room temperature for 1 hr. A solution of 8.83 g (0.0283 mole) of N,N-diethyl-N'-[2-(phenylsulfonyl)ethyl]-1,4-butanediamine in 50 ml of tetrahydrofuran was added, and the mixture was refluxed for 16 hr. The solvent was removed in vacuo, and the residue was partitioned between methylene chloride and water. The methylene chloride solution was dried over sodium sulfate, and the solvent was removed in vacuo to give the free base of the title compound. This was converted to the dicitrate salt, and the salt was recrystallized from methanol-diethyl ether to give 20.88 g (89.5%) of the title compound, a white, crystalline solid, m.p. 98°–101° C.

Analysis: Calculated for $C_{35}H_{59}N_4O_{17.5}S$: C 49.58; H, 7.01; N, 6.61. Found: C, 49.48; H, 6.95; N, 6.63.

EXAMPLE 19

N,N-Bis[2-(dimethylamino)ethyl]-N'-(1-methylethyl)-N'-[2-(2-naphthalenylthio)ethyl]urea, citrate The title compound is prepared utilizing the procedure of Method D. The compound, 1-methyl-N-[2-(2-naphthalenylthio)ethyl]ethanamine (oil in preparation 14), and excess phosgene are reacted in methylene chloride plus Proton Sponge ®. After being extracted (washing) with dilute sulfuric acid, the organic layer is dried and evaporated to give an oil. The oil is dissolved in tetrahydrofuran and reacted with N'-[2-(dimethylamino)ethyl]-N,N-dimethyl-1,2-ethanediamine (excess).

The reaction mixture is stripped to dryness, and the residue partitioned between water and methylene chloride. Evaporation of the solvent yields an oil which may or may not crystallize. Treatment with citric acid followed by recrystallization from methanol/diethyl ether gives the title compound.

EXAMPLE 20

N,N-Bis[2-(diethylamino)ethyl]-N'-(1-methylethyl)-N'-[2-4-nitrophenyl)sulfonyl]ethylurea maleate The title compound is prepared by Method D and the procedure of Example 19, by reacting in sequence:

1-methyl-N-[2-[(4-nitrophenyl)sulfonyl]ethyl]ethanamine (oil in Preparation 16), phosgene (excess), Proton Sponge ®, N'-[2-(diethylamino)ethyl]-N,N-diethyl-1,2-ethanediamine (excess) and treating with malic acid.

EXAMPLE 21

N,N-Bis[2-(dipropylamino)ethyl]-N'-(1-methylethyl)-N'-[2-[(4-methylphenyl)thio]ethyl]urea citrate The title compound is prepared by Method D and the procedure of Example 19, by reacting in sequence:

1-methyl-N-[2-[(4-methylphenyl)thio]ethyl]ethanamine (oil obtained in Preparation 17), phosgene (excess), Proton Sponge ®, N'-[2-(dipropylamino)ethyl-N,N-dipropyl-1,2-ethanediamine (excess), and treating with citric acid.

EXAMPLE 22

N,N-Bis[3-(dimethylamino)propyl]-N'-[2-[(2-furanylmethyl)thio]ethyl]-N'-(1-methylethyl)urea oxalate The title compound is prepared by Method D and the procedure of Example 19, by reacting in sequence:

N-[2-[(2-furanylmethyl)thio]ethyl]-2-propanamine, phosgene (excess) Proton Sponge ®, N'-[3-(dimethylamino)propyl]-N,N-dimethyl-1,3-propanediamine (excess), and treating with oxalic acid.

EXAMPLE 23

N,N-Bis[3-(dimethylamino)propyl]-N'-[2-[(2-furanylmethyl)sulfonyl]ethyl]-N'-(1-methylethyl)urea oxalate The title compound is prepared by Method D and the procedure of Example 19, by reacting in sequence:

N-[2-[(2-furanylmethyl)sulfonyl]ethyl]-2-propanamine, phosgene (excess), Proton Sponge ®, N'-[3-(dimethylamino)propyl]-N,N-dimethyl-1,3-propanediamine (excess), and treating with oxalic acid.

EXAMPLE 24

N,N-Bis[3-(dimethylamino)propyl]-N'-[2-[(2-furanylmethyl)sulfinyl]ethyl]-N'-(1-methylethyl)urea oxalate The title compound is prepared by Method D and the procedure of Example 19, by reacting in sequence:

N-[2-[(2-furanylmethyl)sulfinyl]ethyl]-2-propanamine, phosgene (excess), Proton Sponge ®, N'-[3-(dimethylamino)propyl]-N,N-dimethyl-1,3-propanediamine (excess), and treating with oxalic acid.

EXAMPLE 25

N,N-Bis[3-(diethylamino)propyl]-N'-(1-methylethyl)-N'-[2-(phenylsulfonyl)ethyl]urea fumarate The title compound is prepared by Method D and the procedure of Example 19, by reacting in sequence:

1-methyl-N-[2-(phenylsulfonyl)ethyl]ethanamine (oil obtained in Preparation 21), phosgene (excess), Proton Sponge ®, N'-[3-(diethylamino)propyl]-N,N-diethyl-1,3-propanediamine (excess), and treating with fumaric acid.

EXAMPLE 26

N-[2-[[4-(Dimethylamino)phenyl]sulfonyl]ethyl]-N'N'-bis[3-(dipropylamino)propyl]-N-(1-methylethyl)urea hydrochloride The title compound is prepared by Method D and the procedure of Example 19, by reacting in sequence:

N-[2-[(4-dimethylaminophenyl)sulfonyl]ethyl]2-propanamine, phosgene (excess), Proton Sponge ®, N'-[3-(dipropylamino)propyl]-N,N-dipropyl-1,3-propanediamine (excess), and treating with hydrochloric acid.

EXAMPLE 27

N-[2-[(4-chlorophenyl)sulfonyl]ethyl]-N-(1-methylethyl)-N',N'-bis[2-(4-morpholinyl)ethyl urea oxalate The title compound is prepared by Method D and the procedure of Example 19, by reacting in sequence:

N-[2-[(4-chlorophenyl)sulfonyl]ethyl]-1-methylethanamine (oil obtained in Preparation 23), phosgene (excess), Proton Sponge ®, 1-(4-morpholinyl)-N-[2-(4-morpholinyl)ethyl]ethanamine, sodium carbonate, and treating with oxalic acid.

EXAMPLE 28

N-[2-[(2,3-Dihydro-1H-inden-4-yl)sulfonyl]ethyl]-N-(1-methylethyl)-N',N'-bis[3-(4-morpholinyl)propyl]urea maleate The title compound is prepared by Method D and the procedure of Example 19, by reacting in sequence:

N-[2-[(2,3-dihydro-1H-inden-4-yl)sulfonyl]ethyl]-1-methyl ethanamine, phosgene (excess), Proton Sponge ®, 1-(4-morpholinyl)-N-[3-(4-morpholinyl)propyl]propanamine, sodium carbonate, and treating with malic acid.

EXAMPLE 29

N-[2-[(2,3-Dihydro-1H-inden-5yl)sulfonyl]ethyl]-N-(1-methylethyl)-N',N'-bis[2-(4-phenyl-1-piperazinyl)ethyl]urea citrate The title compound is prepared by Method D and the procedure of Example 19, by reacting in sequence:

N-[2-[(2,3-dihydro-1H-inden-5-yl)sulfonyl]ethyl]-1-methyl ethanamine, phosgene (excess), Proton Sponge®, 2-[1-(4-phenyl)piperazinyl]-N-[2-[1-(4-phenyl)-piperazinyl]ethyl]ethanamine (excess), and treating with citric acid.

EXAMPLE 30

N-[2-[(4-Ethoxyphenyl)sulfonyl]ethyl]-N-(1-methylethyl)-N',N'-bis[3-(4-phenyl-1-piperazinyl)propyl]urea fumarate The title compound is prepared by Method D and the procedure of Example 19, by reacting in sequence:
N-[2-[(4-ethoxyphenyl)sulfonyl]ethyl]-2-propanamine (oil obtained in Preparation 24), phosgene (excess), Proton Sponge®, 3-[1-(4-phenyl)piperazinyl]-N-[3-[1-(4-phenyl)piperazinyl]propyl]-1-propanamine (excess), and treating with fumaric acid.

EXAMPLE 31

N-[2-[(4-Methoxyphenyl)sulfonyl]ethyl]-N-(1-methylethyl)-N',N'-bis[2-(4-methyl-1-piperazinyl)ethyl]urea oxalate The title compound is prepared by Method D and the procedure of Example 19, by reacting in sequence:
N-[2-[(4-methoxyphenyl)sulfonyl]ethyl]-2-propanamine (oil obtained in Preparation 25), phosgene (excess), Proton Sponge®, 2-[1-(4-methyl)piperazinyl]-N-[2-[1-(4-methyl)piperazinyl]ethyl]ethanamine, sodium carbonate, and treating with oxalic acid.

EXAMPLE 32

N-[2-(3,4-dichlorophenoxy)ethyl]-N-(1-methylethyl)-N',N'-[3-(4-methyl-1-piperazinyl)propyl]urea oxalate The title compound is prepared by Method D and the procedure of Example 19, by reacting in sequence:
N-[2-(3,4-dichlorophenoxy)ethyl]-N-1-methylethanamine (oil obtained in Preparation 26), phosgene (excess), Proton Sponge®, 3-[1-(4-methyl)piperazinyl]-N-[3-[1-(4-methyl)piperazinyl]propyl]-1-propanamine, sodium carbonate, and treating with oxalic acid.

EXAMPLE 33

N-[2-[(3,4-Dichlorophenyl)thio]ethyl]-N-(1-methylethyl)-N',N'-bis[2-(1-pyrrolidinyl)ethyl]urea citrate The title compound is prepared by Method D and the procedure of Example 19, by reacting in sequence:
N-[2-[(3,4-dichlorophenyl)thio]ethyl]-2-propanamine (clear oil obtained in Preparation 27, Part B), phosgene (excess), Proton Sponge®, 2-(1-pyrrolidinyl)-N-[2-(1-pyrrolidinyl)ethyl]ethanamine, sodium carbonate, and treating with citric acid.

EXAMPLE 34

N'-[2-(2-Pyridinyl)ethyl]-N,N-bis[2-(1-pyrrolidinyl)ethyl]thiourea oxalate

The title compound is prepared utilizing the procedure of Method C. The compound 2-(2-aminoethyl)-pyridine (starting compound in Preparation 28) and 1,1'-thiocarbonyldiimidazole are reacted in tetrahydrofuran solvent at room temperature for approximately one hour. To the above solution is added 2-(1-pyrrolidinyl)-N-[2-(1-pyrrolidinyl)ethyl]ethanamine in a tetrahydrofuran solvent, and the mixture refluxed for approximately 16 hours. Solvent is removed by evaporation and the residue partitioned between methylene chloride and water. The methylene chloride layer is then dried over magnesium sulfate and the solvent removed by evaporation, to give the free base of the title compound. Treatment with oxalic acid followed by recrystallization from methanol/diethyl ether gives the title compound.

EXAMPLE 35

N-(2-Phenoxyethyl)-N-(2-phenylethyl)-N',N'-bis[2-(1-pyrrolidinyl)ethyl]urea citrate P The title compound is prepared by Method D and the procedure of Example 19, by reacting in sequence:
N-(3-phenoxypropyl)benzeneethanamine (oil obtained in Preparation 29), phosgene (excess), Proton Sponge®, 2-(1-pyrrolidinyl)-N-[2-(1-pyrrolidinyl)ethyl]ethanamine, sodium carbonate, and treating with citric acid.

EXAMPLE 36

N-[2-(4-Acetylphenoxy)ethyl]-N-(1-methylethyl)-N',N'-bis[3-(1-pyrrolidinyl)propyl]urea maleate The title compound is prepared by Method D and the procedure of Example 19, by reacting in sequence:
2-(4-acetylphenoxy)-N-(1-methylethyl)ethanamine, phosgene (excess), Proton Sponge®, 3-(1-pyrrolidinyl)-N-[3-(1-pyrrolidinyl)propyl]-1-propanamine, sodium carbonate, and treating with malic acid.

EXAMPLE 37

N,N-Bis[2-(dimethylamino)ethyl]-N'-(1-methylethyl)-N'[2-(4-nitrophenoxy)-ethyl]urea fumarate The title compound is prepared by Method D and the procedure of Example 19, by reacting in sequence:
N-(1-methylethyl)-2-(4-nitrophenoxy)ethanamine (oil obtained in Preparation 31), phosene (excess), Proton Sponge®, N'[2-(dimethylamino)ethyl]-N,N-dimethyl-1,2-ethanediamine (excess), and treating with fumaric acid.

EXAMPLE 38

N-[2-[(3,5-Dichlorophenyl)sulfonyl]ethyl]-N-(1-methylethyl)-N',N'-bis[2-(4-morpholinyl)ethyl]urea hydrochloride The title compound is prepared by Method D and the procedure of Example 19, by reacting in sequence:
N-[2-[(3,5-dichlorophenyl)sulfonyl]ethyl]-1-methylethanamine, phosgene (excess), Proton Sponge®, 2-(4-morpholinyl)-N-[2-(4-morpholinyl)ethyl]ethanamine, sodium carbonate, and treating with hydrochloric acid.

EXAMPLE 39

N-(1-Methylethyl)-N',N'-bis[2-(4-morpholinyl)ethyl]-N-[2-[(3,4,5-trimethoxyphenyl)sulfonyl]ethyl]urea citrate The title compound is prepared by Method D and the procedure of Example 19, by reacting in sequence:
N-[2-[(3,4,5-trimethoxyphenyl)sulfonyl]ethyl]-1-methylethanamine, phosgene (excess), Proton Sponge®, 2-(4-morpholinyl)-N-[2-(4-morpholinyl)ethyl]ethanamine, sodium carbonate, and treating with citric acid.

EXAMPLE 40

N-(1-Methylethyl)-N',N'-bis[2-(4-morpholinyl)ethyl]-N-[2-[[4-(trifluoromethyl)phenyl]sulfonyl]ethyl]urea oxalate The title compound is prepared by Method D and the procedure of Example 19, by reacting in sequence:

1-methyl-N-[2-[(4-trifluoromethylphenyl)sulfonyl]ethyl]ethanamine, phosene (excess), Proton Sponge®, 2-(4-morpholinyl)-N-[2-(4-morpholinyl)ethyl]ethanamine, sodium carbonate, and treating with oxalic acid.

EXAMPLE 41

N-[2-[(4-Cyanophenyl)sulfonyl]ethyl]-N-(1-methylethyl)-N',N'-bis[2-(4-morpholinyl)ethyl]urea hydrochloride The title compound is prepared by Method D and the procedure of Example 19, by reacting in sequence:
N-[2-[(4-cyanophenylsulfonyl)ethyl-1-methylethanamine, phosgene (excess), Proton Sponge®, 2-(4-morpholinyl)-N-[2-(4-morpholinyl)ethyl]ethanamine, sodium carbonate, and treating with hydrochloric acid.

EXAMPLE 42

N-(1-Methylethyl)-N',N'-bis[2-(4-morpholinyl)ethyl]-N-[2-(4-nitrophenyl)sulfonyl]ethyl]urea maleate The title compound is prepared by Method D and the procedure of Example 19, by reacting in sequence:
1-methyl-N-[2-[(4-nitrophenyl)sulfonyl]ethyl]ethanamine, phosgene (excess), Proton Sponge®, 2-(4-morpholinyl)-N-[2-(4-morpholinyl)ethyl]ethanamine, sodium carbonate, and treating with malic acid.

EXAMPLE 43

N,N-Bis[2-(diethylamino)ethyl]-N'-(1-methylethyl)-N'-[2-(1-naphthalenylthio)ethyl]thiourea oxalate The title compound is prepared by Method D and the procedure of Example 19, by reacting in sequence:
1-methyl-N-[2-(1-naphthalenylthio)ethyl]ethanamine (oil obtained in Preparation 33), phosgene (excess), Proton Sponge®, N'-[2-(diethylamino)ethyl]-N,N-diethyl-1,2-ethanediamine (excess), and treating with oxalic acid.

EXAMPLE 44

N-[2-[[4-[2-(Dimethylamino)ethoxy]phenyl]sulfonyl]ethyl]-N-(1-methylethyl)-N',N'-bis[2-(dipropylamino)ethyl]urea oxalate The title compound is prepared by Method D and the procedure of Example 19, by reacting in sequence:
N-[2-[[4-[2-(dimethylamino)ethoxy]phenyl]sulfonyl]ethyl]-2-propanamine (liquid obtained in Preparation 34), phosgene (excess), Proton Sponge®, N'-[2-(dipropylamino)ethyl]-N,N-dipropyl-1,2-ethanediamine (excess), and treating with oxalic acid.

EXAMPLE 45

N,N-Bis[3-(dimethylamino)propyl]-N'-(1-methylethyl)-N'-[2-[4-(methylsulfonyl)phenoxy]ethyl]urea fumarate The title compound is prepared by Method D and the procedure of Example 19, by reacting in sequence:
N-[2-[4-(methylsulfonyl)phenoxy]ethyl]-2-propanamine (free base obtained in Preparation 37), phosgene (excess), Proton Sponge®, N'-[3-(dimethylamino)propyl]-N,N-dimethyl-1,3-propanediamine (excess), and treating with fumaric acid.

EXAMPLE 46

N,N-Bis[3-(diethylamino)propyl]-N'-(1-methylethyl)-N'-[2-[4-(methylthio)phenoxy]ethyl]urea citrate The title compound is prepared by Method D and the procedure of Example 19, by reacting in sequence:
N-[2-[4-(methylthio)phenoxy]ethyl]-2-propanamine (oil obtained in Preparation 38), phosgene (excess), Proton Sponge®, N'-[3-(diethylamino)propyl]-N,N-diethyl-1,3-propanediamine (excess), and treating with citric acid.

EXAMPLE 47

N,N-Bis[3-(dipropylamino)propyl]-N'-(1-methylethyl)-N'-[2-[4-(methylsulfinyl)phenoxy]ethyl]thiourea citrate The title compound is prepared by Method D and the procedure of Example 19, by reacting in sequence:
N-[2-[4-(methylsulfinyl)phenoxy]-2-propanamine (oil obtained in Preparation 39), thiophosgene (excess), Proton Sponge®, N'-[3-(dipropylamino)propyl]-N,N-(dipropyl)1,3-propanediamine (excess), and treating with citric acid.

EXAMPLE 48

Following the procedure of Example 2 and substituting the following for N,N-diethyl-N'-[2-(phenylsulfonyl)ethyl]-1,2-ethanediamine:
(a) N-[4-[3-[[2-(diethylamino)ethyl]amino]propoxy]phenyl]acetamide,
(b) 1-[4-[3-[[2-(diethylamino)ethyl]amino]propoxy]-3-methoxyphenyl]ethanaone, and
(c) 4-[4-[[2-(diethylamino)ethyl]amino]propoxy]benzamide,
there are obtained:
(a) N-[3-[4-(acetylamino)phenoxy]propyl]-N,N'-bis[2-(diethylamino)ethyl]urea oxalate,
(b) N-[3-[4-(4-acetyl-2-methoxyphenoxy)propyl]-N,N'-bis[2-(diethylamino)ethyl]urea oxalate, and
(c) N-[4-(4-aminocarbonylphenoxy)butyl]-N,N'-bis[2-(diethylamino)ethyl]urea oxalate.

EXAMPLE 49

N'''-Cyano-N'-[2-(diethylamino)ethyl]-N-[3-(diethylamino)propyl]-N-[2-(phenylsulfonyl)ethyl]quanidine citrate hydrate [1:2:0.5]

A solution of 8.05 g (0.0203 mole) of N'-Cyano-N-[3-(diethylamino)propyl]-N-[2-(phenylsulfonyl)ethyl]carbamimidothioic acid methyl ester (free base in Preparation 45) and 2.67 g (0.0230 mole) of N,N-diethylethylenediamine in 500 ml of acetonitrile was refluxed for 10 days. The solvent was removed in vacuo and the residue was partitioned between methylene chloride and water. The methylene chloride solution was dried over magnesium sulfate, and the solvent was removed in vacuo to give an oil. This was subjected to flash chromatography (silica gel, eluted with methanol and then gradiently eluted with methanol-ammonium hydroxide) to give 4.77 g of an oil. This was dissolved in methanol, 2 equivalents of citric acid were added, and anhydrous diethyl ether was added until the solution became slightly cloudy. A white preciitate was collected to give 7.03 g (40.4%) of the title compound as a white crystalline solid; m.p. 102°–105° C., with decomposition.

Analysis: Calculated for $C_{35}H_{57}N_6O_{16.5}S$: C, 49.00; H, 6.70; N, 9.80. Found: C, 49.34; H, 6.81; N, 9.46.

EXAMPLE 50

Following the procedure of Example 36 and substituting the following for 2-(4-acetylphenoxy)-N-(1-methylethyl)ethanamine:
(a) 4-methyl-N-(3-phenoxypropyl)benzeneamine,
(b) 3-bromo-N-(3-phenoxypropyl)benzeneamine, (c) 2,4,6-tribromo-N-(3-phenoxypropyl)benzeneamine, (d) 4-methoxy-N-(3-phenoxypropyl)benzeneamine, (e) 4-nitro-N-(3-phenoxypropyl)benzeneamine (f) N-(3-phenoxypropyl)-3-(trifluoromethyl)benzeneamine, and (g) 4-[(3-phenoxypropyl)amino]benzonitrile
there are obtained:

(a) N-(4-methylphenyl)-N-(3-phenoxypropyl)-N',N'-bis[3-(1-pyrrolidinyl)propyl]urea maleate, (b) N-(3-bromophenyl)-N-(3-phenoxypropyl)N',N'-bis[3-(1-pyrrolidinyl)propyl]urea maleate, (c) N-(3-phenoxypropyl)-N',N'-bis[3-(1-pyrrolidinyl)propyl]-N-(2,4,6-tribromophenyl)urea maleate, (d) N-(4-methoxyphenyl)-N-(3-phenoxypropyl)-N',N'-bis[3-(1-pyrrolidinyl)propyl]urea maleate, (e) N-(4-nitrophenyl)-N-(3-phenoxypropyl)-N',N'-bis[3-(1-pyrrolidinyl)propyl]urea maleate, (f) N-(3-phenoxypropyl)-N',N'-bis[3-(1-pyrrolidinyl)propyl]-N-[3-(trifluoromethyl)phenyl]urea maleate, and (g) N-(4-cyanophenyl)-N-(3-phenoxypropyl)-N',N'-bis{3-(1-pyrrolidinyl)propyl]urea maleate.

EXAMPLE 51

Following the procedure of Example 19 and substituting the following for 1-methyl-N-[2-(2-naphthalenylthio)ethyl]ethanamine:

(a) 2-(phenylsulfonyl)ethanamine, and (b) 1-methyl-N-[2-(phenylsulfonyl)ethyl]ethanamine, there are obtained:

(a) N,N-bis[2-(dimethylamino)ethyl]-N'-[2-(phenylsulfonyl)ethyl]urea citrate and (b) N,N-bis[2-(dimethylamino)ethyl]-N'-(1-methylethyl)-N'-[2-(phenylsulfonyl)ethyl]urea citrate.

EXAMPLE 52

N''-Cyano-N',N'-bis[2-(dimethylamino)ethyl]-N-(1-methylethyl)-N-[2-(phenylsulfonyl)ethyl]guanidine citrate The title compound is prepared utilizing the procedure of Method F. N'-[2-(dimethylamino)ethyl]-N,N-dimethyl-1,2-ethanediamine is reacted with dimethyl-N-cyanodithioiminocarbonate in absolute ethanol solvent. After stirring at room temperature for 16–20 hours and refluxing for 4–8 hours, solvent is removed in vacuo to give an oil residue. This residue is then partitioned between water and methylene chloride, the methylene chloride layer is then stripped to dryness over magnesium sulfate and solvent removed in vacuo to give an oil which is then reacted with N-[2-(phenylsulfonyl)ethyl]-2-propanamine in acetonitrile solvent, and refluxed for 2–10 days. The solvent is removed in vacuo and the residue partitioned between methylene chloride and water. The methylene chloride solution is dried over magnesium sulfate and the solvent removed in vacuo to give an oil. The oil is then subjected to flash chromatography and the desired fraction collected. Dissolving the oil in methanol and treating it with citric acid followed by recrystallization gives the title compound.

EXAMPLE 53

Following the procedure of Example 49 and substituting the following for N'-cyano-N-[3-(diethylamino)propyl]-N-[2-(phenylsulfonyl)ethyl]carbamimidothioic acid methyl ester:

(a) N'-cyano-N-[2-(diethylamino)ethyl]-N-[2-(phenylsulfinyl)ethyl]carbamimidothioic acid methyl ester, (b) N'-cyano-N-[2-(diethylamino)ethyl]-N-(3-phenylpropyl)carbamimidothioic acid methyl ester, (c) N'-cyano-N-[2-(diethylamino)ethyl]-N-[2-(phenylthio)ethyl]carbamimidothioic acid methyl ester, and (d) N'-cyano-N-[2-(diethylamino)ethyl]-N-(2-phenoxyethyl)carbamimidothioic acid methyl ester
there are obtained:

(a) N''-cyano-N,N'-bis[2-(diethylamino)ethyl]-N-[2-(phenylsulfinyl)ethyl]guanidine citrate, (b) N''-cyano-N,N'-bis[2-(diethylamino)ethyl]-N-(3-phenylpropyl)guanidine citrate, (c) N''-cyano-N,N'-bis[2-(diethylamino)ethyl]-N-[2-(phenylthio)ethyl]guanidine citrate, and (d) N''-cyano-N,N'-bis[2-(diethylamino)ethyl]-N-(2-phenoxyethyl)guanidine.

EXAMPLE 54

Following the procedure of Example 52 and substituting the following for N-[2-(phenylsulfonyl)ethyl]-2-propanamine:

(a) 1-methyl-N-[2-[(4-methylphenyl)thio]ethyl]ethanamine (oil obtained in Preparation 17), (b) N-[2-[(2-furanylmethyl)sulfinyl]ethyl]-2-propanamine, (c) 2-(2-aminoethyl)pyridine (starting compound in Preparation 28), and (d) N-(1-methylethyl)-2-(4-nitrophenoxy)ethanamine (oil obtained in Preparation 31).
there are obtained:

(a) N''-cyano-N',N'-bis[2-(dimethylamino)ethyl]-N-(1-methylethyl)-N-[2-[(4-methylphenyl)thio]ethyl]guanidine citrate, (b) N''-cyano-N',N'-bis[2-(dimethylamino)ethyl]-N-[2-[(2-furanylmethyl)sulfinyl]ethyl]-N-(1-methylethyl)guanidine citrate, (c) N''-cyano-N',N'-bis[2-(dimethylamino)ethyl]-N-[2-(2-pyridinyl)ethyl]guanidine citrate, and (d) N''-cyano-N',N'-bis[2-(dimethylamino)ethyl]-N-[2-(4-nitrophenoxy)ethyl]-N-(1-methylethyl)guanidine citrate.

EXAMPLE 55

N'-[2-(Diethylamino)ethyl]-N-[3-(diethylamino)propyl]-N-[2-(phenylsulfonyl)ethyl]thiourea citrate The title compound is prepared by Method B, and the procedure of Example 1 by reacting in sequence:

1,1'-thiocarbonyldiimidazole, N,N-diethylaminoethylamine, and N,N-diethyl-N'-[2-(phenylsulfonyl)ethyl]-1,3-propanediamine
to give the free base of the title compound which is then reacted with citric acid to give the title compound.

EXAMPLE 56

N,N'-Bis[2-(diethylamino)ethyl]-N-(2-phenoxyethyl)thiourea citrate

The title compound is prepared by Method B, and the procedure of Example 13 by reacting in sequence:

1,1'-thiocarbonyldiimidazole, N,N-diethylaminoethylamine, and N,N-diethyl-N'-2-(phenoxyethyl)-1,2-ethanediamine
to give the free base of the title compound which is then reacted with citric acid to give the title compound.

EXAMPLE 57

N,N'-Bis[2-(diethylamino)ethyl]-N-[2-(phenylthio)ethyl]thiourea citrate

The title compound is prepared by Method B, and the procedure of Example 14 by reacting in sequence:
1,1'-thiocarbonyldiimidazole, N,N-diethylaminoethylamine, and N,N-diethyl-N'-[2-(phenylthio)ethyl]-1,2-ethanediamine
to give the free base of the title compound which is then reacted with citric acid to give the title compound.

EXAMPLE 58

N,N'-Bis[2-(diethylamino)ethyl]-N-(3-phenylpropyl)thiourea citrate

The title compound is prepared by Method B, and the procedure of Example 15 by reacting in sequence:
1,1'-thiocarbonyldiimidazole, N,N-diethylaminoethylamine, and N,N-diethyl-N'-[3-(phenylpropyl)-1,2-ethanediamine
to give the free base of the title compound which is then reacted with citric acid to give the title compound.

EXAMPLE 59

N,N'-Bis[2-(diethylamino)ethyl]-N-[2-(phenylsulfinyl)ethyl]thiourea citrate

The title compound is prepared by Method B, and the procedure of Example 16 by reacting in sequence:
1,1'-thiocarbonyldiimidazole, N,N-diethylaminoethylamine, and N,N-diethyl-N'-[2-(phenylsulfinyl)ethyl-1,2-ethanediamine
to give the free base of the title compound which is then reacted with citric acid to give the title compound.

EXAMPLE 60

N,N-Bis[3-(dimethylamino)propyl]-N'-[2-[(2-furanylmethyl)sulfinyl]ethyl]-N'-(1-methylethyl)thiourea citrate The title compound is prepared by Method D, and the procedure of Example 19 by reacting in sequence:
N-[2-[(2-furanylmethyl)sulfinyl]ethyl]-2-propanamine, thiophosgene (excess), Proton Sponge®, and N'-[3-(dimethylamino)propyl]-N,N-dimethyl-1,3-propanediamine (excess).
to give the free base of the title compound which is then reacted with citric acid to give the title compound.

EXAMPLE 61

N-[2-[(3,5-Dichlorophenyl)sulfonyl]ethyl]-N-(1-methylethyl)-N',N'-bis[2-(4-morpholinyl)ethyl]thiourea citrate The title compound is prepared by Method D, and the procedure of Example 19 by reacting in sequence:
N-[2-[(3,5-dichlorophenyl)sulfonyl]ethyl]-1-methylethanamine, thiophosgene (excess), Proton Sponge®, 2-(4-morpholinyl)-N-[2-(4-morpholinyl)ethyl]ethanamine, and sodium carbonate
to give the free base of the title compound which is then reacted with citric acid to give the title compound.

EXAMPLE 62

N-[2-(2-Pyridinyl)ethyl]-N',N'-bis[2-(1-pyrrolidinyl)ethyl]urea citrate

The title compound is prepared by Method C, and the procedure of Example 34 by reacting in sequence:
1,1'-carbonyldiimidazole, 2-(2-aminoethyl)pyridine, and 2-(1-pyrrolidinyl)-N-[2-(1-pyrrolidinyl)ethyl]ethanamine
to give the free base of the title compound which is then reacted with citric acid to give the title compound.

EXAMPLE 63

N,N-Bis[2-(diethylamino)ethyl]-N'-(1-methylethyl)-N'-[2-(phenylsulfonyl)ethyl]urea A mixture of 7.67 g (0.0265 mole) of N-(1-methylethyl)-N-[2-(phenylsulfonyl)ethyl]carbamic chloride and 6.24 g (0.029 mole) of N'-[2-(diethylamino)ethyl]-N,N-diethyl-1,2-ethanediamine and 2.73 g (0.0270 mole) of triethylamine in 400 ml of tetrahydrofuran was refluxed for 6 hr and then was stirred at room temperature for 7 hr. The solvent was removed in vacuo and the residue was partitioned between methylene chloride and dilute sodium hydroxide. The methylene chloride solution was dried over sodium sulfate, and the solvent was removed in vacuo to give an oil. This was dissolved in ether, and the solution was extracted with three portions of water. The ether solution was dried over sodium sulfate, and the solvent was removed in vacuo to give an oil. This was pumped under high vacuum at 56° C. for 20 hr to give the title compound as an oil.

Analysis: Calculated for $C_{24}H_{44}N_4O_3S$: C, 61.50; H, 9.46; N, 11.95. Found: C, 61.24; H, .952; N, 11.79.

$^1$HNMR (CDCl$_3$)δ8.00–7.74(m, 2H, ortho aromatic), 7.70–7.33(m, 3H, aromatic), 3.75(m, 1H, i-C$_3$H$_7$), 3.45–3.00(m, 8H, SO$_2$CH$_2$CH$_2$ and N(CH$_2$CH$_2$N(CH$_2$CH$_3$)$_2$)$_2$), 2.84–2.28(m, 12H, N(CH$_2$CH$_2$N(CH$_2$CH$_3$)$_2$)$_2$), 1.20–0.80(m, 18H, CH$_3$).

EXAMPLE 64

N,N-Bis[2-(diethylamino)ethyl]-N'-[2-(phenylsulfonyl)ethyl]urea

A mixture of 4.84 g (0.0262 mole) of 2-phenylsulfonylethylamine and 4.90 g (0.030 mole) of 1,1'-carbonyldiimidazole in 400 ml of tetrahydrofuran was stirred at room temperature for 1 hr. A solution of 5.90 g (0.027 mole) of N'-[2-(diethylamino)ethyl]-N,N-diethyl-1,2-ethanediamine in 50 ml of tetrahydrofuran was added, and the solution was refluxed for 16 hr. The solvent was removed in vacuo, and the residue was partitioned between methylene chloride and water. The methylene chloride solution was dried over sodium sulfate, and the solvent was removed in vacuo to give an oil. This was subjected to column chromatography (silica gel, gradiently eluted with methylene chloride-methanol) to give 7.64 g (60.78) of the title compound as an oil.

Analysis: Calculated for $C_{21}H_{38}N_4O_3S$: C, 59.12; H, 8.98; N, 13.13. Found: C, 58.93; H, 9.13; N, 13.10. C, 58.89; H, 9.14; N, 13.03.

$^1$HNMR (CDCl$_3$)δ8.30(br s, H, NH), 8.00–7.73(m, 2H, ortho aromatic), 7.70–7.38(m, 3H, aromatic), 3.54–3.05(m, 8H, SO$_2$CH$_2$CH$_2$ and N(CH$_2$CH$_2$NEt$_2$)$_2$), 2.77–2.28(m, 12H, N(CH$_2$CH$_2$N(CH$_2$CH$_3$)$_2$)$_2$), 1.18–0.80(t, 12H, CH$_3$).

TABLE 1

| Ex No. | Ar | x | d | n | Z | B | W | P | —N(R³)(R⁴) | Salt-Hydrate |
|---|---|---|---|---|---|---|---|---|---|---|
| 1 | C₆H₅— | SO₂ | 1 | 2 | —(CH₂)₂—N(C₂H₅)₂ | carbonyl | H | 2 | —N(C₂H₅)₂ | oxalate [1:2] |
| 2 | C₆H₅— | SO₂ | 1 | 2 | —(CH₂)₂—N(C₂H₅)₂ | carbonyl | H | 2 | —N(C₂H₅)₂ | oxalate [1:2] |
| 3 | C₆H₅— | SO₂ | 1 | 2 | —(CH₂)₂—C₄H₈NO[a] | carbonyl | H | 2 | —N(C₄H₈NO)[a] | oxalate hydrate [1:2:1] |
| 4 | C₆H₅— | SO₂ | 1 | 2 | —(CH₂)₂—C₄H₈N[b] | carbonyl | H | 2 | —N(C₂H₅)₂ | oxalate hydrate [1:2:0.5] |
| 5 | C₆H₅— | SO₂ | 1 | 2 | —(CH₂)₂—N(C₂H₅)₂ | carbonyl | H | 2 | —N(C₆H₅)(CH₃) | fumarate [1:1] |
| 6 | C₆H₅— | SO₂ | 1 | 2 | —(CH₂)₂—C₆H₁₂N[c] | carbonyl | H | 2 | —N(C₂H₅)₂ | oxalate hydrate [1:2:0.5] |
| 7 | C₆H₅— | SO₂ | 1 | 2 | —(CH₂)₂—N(C₂H₅)₂ | carbonyl | H | 3 | —N(C₂H₅)₂ | oxalate hydrate [1:2:0.5] |
| 8 | C₆H₅— | SO₂ | 1 | 2 | —(CH₂)₂—N(C₆H₅)(CH₃) | carbonyl | H | 2 | —N(C₂H₅)₂ | oxalate hydrate [1:1:0.5] |
| 9 | C₆H₅— | SO₂ | 1 | 2 | —(CH₂)₂—C₅H₁₀N[d] | carbonyl | H | 2 | —N(C₂H₅)₂ | oxalate hydrate [1:2:1] |
| 10 | C₆H₅— | SO₂ | 1 | 2 | —(CH₂)₂—N(C₂H₅)₂ | carbonyl | H | 2 | —N(C₂H₅)₂ | oxalate hydrate [1:2:0.5] |
| 11 | C₆H₅— | SO₂ | 1 | 2 | —(CH₂)₂—N(C₂H₅)₂ | carbonyl | H | 2 | —C₅H₁₀N[e] | citrate [1:2] |
| 12 | C₆H₅— | SO₂ | 1 | 2 | —(CH₂)₂—N(C₂H₅)₂ | carbonyl | H | 3 | —N(C₂H₅)₂ | oxalate [1:2] |
| 13 | C₆H₅— | O | 1 | 2 | —(CH₂)₂—N(C₂H₅)₂ | carbonyl | H | 2 | —N(C₂H₅)₂ | citrate [1:2] |
| 14 | C₆H₅— | S | 1 | 2 | —(CH₂)₂—N(C₂H₅)₂ | carbonyl | H | 2 | —N(C₂H₅)₂ | citrate [1:2] |
| 15 | C₆H₅— | — | 0 | 3 | —(CH₂)₂—N(C₂H₅)₂ | carbonyl | H | 2 | —N(C₂H₅)₂ | citrate hydrate [1:2:0.5] |
| 16 | C₆H₅— | S(O) | 1 | 2 | —(CH₂)₃—N(C₂H₅)₂ | carbonyl | H | 2 | —N(C₂H₅)₂ | citrate hydrate [1:2:0.5] |
| 17 | C₆H₅— | SO₂ | 1 | 2 | —(CH₂)₃—N(C₂H₅)₂ | carbonyl | H | 3 | —N(C₂H₅)₂ | citrate hydrate [1:2:0.5] |
| 18 | C₆H₅— | SO₂ | 1 | 2 | —(CH₂)₄—N(C₂H₅)₂ | carbonyl | H | 2 | —N(C₂H₅)₂ | citrate hydrate [1:2:0.5] |
| 19 | 2-naphthalenyl | S | 1 | 2 | —CH(CH₃)₂ | carbonyl | —(CH₂)₂N(CH₃)₂ | 2 | —N(CH₃)₂ | citrate |
| 20 | 4-NO₂—C₆H₄— | SO₂ | 1 | 2 | —CH(CH₃)₂ | carbonyl | —(CH₂)₂N(C₂H₅)₂ | 2 | —N(C₂H₅)₂ | maleate |
| 21 | 4-CH₃—C₆H₄— | S | 1 | 2 | —CH(CH₃)₂ | carbonyl | —(CH₂)₂N(C₃H₇)₂ | 2 | —N(C₃H₇)₂ | citrate |
| 22 | (C₄H₉O)—CH₂— | S | 1 | 2 | —CH(CH₃)₂ | carbonyl | —(CH₂)₃—N(CH₃)₂ | 3 | —N(CH₃)₂ | oxalate |
| 23 | (C₄H₉O)—CH₂— | SO₂ | 1 | 2 | —CH(CH₃)₂ | carbonyl | —(CH₂)₃—N(CH₃)₂ | 3 | —N(CH₃)₂ | oxalate |
| 24 | (C₄H₉O)—CH₂— | S(O) | 1 | 2 | —CH(CH₃)₂ | carbonyl | —(CH₂)₃—N(C₂H₅)₂ | 3 | —N(C₂H₅)₂ | fumarate |
| 25 | C₆H₅— | SO₂ | 1 | 2 | —CH(CH₃)₂ | carbonyl | —(CH₂)₃—N(C₃H₇)₂ | 3 | —N(C₃H₇)₂ | hydrochloride |
| 26 | 4-(CH₃)₂N—C₆H₄— | SO₂ | 1 | 2 | —CH(CH₃)₂ | carbonyl | —(CH₂)₂C₄H₈NO[a] | 2 | —C₄H₈NO[k] | oxalate |
| 27 | 4-Cl—C₆H₄— | SO₂ | 1 | 2 | —CH(CH₃)₂ | carbonyl | | | | |

4,895,840

TABLE 1-continued

| Ex No. | Ar | x | d | n | Z | B | W | p | -N(R³)(R⁴) | Salt-Hydrate |
|---|---|---|---|---|---|---|---|---|---|---|
| 28 | 2,3-dihydro-1H-inden-4-yl | SO₂ | 1 | 2 | —CH(CH₃)₂ | carbonyl | —(CH₂)₃—C₄H₈NO⁽ᵍ⁾ | 3 | —C₄H₈NO⁽ᵏ⁾ | maleate |
| 29 | 2,3-dihydro-1H-inden-5-yl | SO₂ | 1 | 2 | —CH(CH₃)₂ | carbonyl | —(CH₂)₂—[4-C₆H₅—C₄H₈N₂]⁽ⁱ⁾ | 2 | 4-C₆H₅—C₄H₈N₂—⁽ˡ⁾ | citrate |
| 30 | 4-C₂H₅O—C₆H₄— | SO₂ | 1 | 2 | —CH(CH₃)₂ | carbonyl | —(CH₂)₃—[4-C₆H₅—C₄H₈N₂]⁽ⁱ⁾ | 3 | 4-C₆H₅—C₄H₈N₂—⁽ˡ⁾ | fumarate |
| 31 | 4-CH₃O—C₆H₄— | SO₂ | 1 | 2 | —CH(CH₃)₂ | carbonyl | —(CH₂)₂—[4-CH₃—C₄H₈N₂]⁽ⁱ⁾ | 2 | 4-CH₃—C₄H₈N₂—⁽ᵐ⁾ | oxalate |
| 32 | 3,4-Cl₂—C₆H₃— | O | 1 | 2 | —CH(CH₃)₂ | carbonyl | —(CH₂)₃—[4-CH₃—C₄H₈N₂]⁽ⁱ⁾ | 3 | 4-CH₃—C₄H₈N₂—⁽ᵐ⁾ | oxalate |
| 33 | 3,4-Cl₂—C₆H₃— | S | 1 | 2 | —CH(CH₃)₂ | carbonyl | —(CH₂)₂—C₄H₈N⁽ᵇ⁾ | 2 | —C₄H₈N⁽ⁿ⁾ | citrate |
| 34 | 2-pyridinyl | — | 0 | 2 | H | thioxo-methyl | —(CH₂)₂—C₄H₈N⁽ᵇ⁾ | 2 | —C₄H₈N⁽ⁿ⁾ | oxalate |
| 35 | C₆H₅— | O | 1 | 2 | —(CH₂)₂—C₆H₅ | carbonyl | —(CH₂)₂—C₄H₈N⁽ᵇ⁾ | 2 | —C₄H₈N⁽ⁿ⁾ | citrate |
| 36 | 4-CH₃C(O)—C₆H₄— | O | 1 | 2 | —CH(CH₃)₂ | carbonyl | —(CH₂)₂—C₄H₈N⁽ᵇ⁾ | 2 | —C₄H₈N⁽ⁿ⁾ | maleate |
| 37 | 4-NO₂—C₆H₄— | O | 1 | 2 | —CH(CH₃)₂ | carbonyl | —(CH₂)₃—N(CH₃)₂ | 3 | —C₄H₈N⁽ⁿ⁾ | fumarate |
| 38 | 3,5-Cl₂—C₆H₃— | SO₂ | 1 | 2 | —CH(CH₃)₂ | carbonyl | —(CH₂)₂—N(CH₃)₂ | 2 | —(CH₂)₂—N(CH₃)₂ | hydrochloride |
| 39 | [3,4,5-(CH₃O)₃—C₆H₂]— | SO₂ | 1 | 2 | —CH(CH₃)₂ | carbonyl | —(CH₂)₂—C₄H₈NO⁽ᵃ⁾ | 2 | —C₄H₈NO⁽ᵏ⁾ | citrate |
| 40 | 4-CF₃—C₆H₄— | SO₂ | 1 | 2 | —CH(CH₃)₂ | carbonyl | —(CH₂)₂—C₄H₈NO⁽ᵃ⁾ | 2 | —C₄H₈NO⁽ᵏ⁾ | oxalate |
| 41 | 4-CN—C₆H₄— | SO₂ | 1 | 2 | —CH(CH₃)₂ | carbonyl | —(CH₂)₂—C₄H₈NO⁽ᵃ⁾ | 2 | —C₄H₈NO⁽ᵏ⁾ | hydrochloride |
| 42 | 4-NO₂—C₆H₄— | SO₂ | 1 | 2 | —CH(CH₃)₂ | carbonyl | —(CH₂)₃—C₄H₈NO⁽ᵃ⁾ | 2 | —C₄H₈NO⁽ᵏ⁾ | maleate |
| 43 | 1-naphthalenyl | S | 1 | 2 | —CH(CH₃)₂ | thioxo-methyl | —(CH₂)₂—C₄H₈NO⁽ᵃ⁾ | 2 | —C₄H₈NO⁽ᵏ⁾ | oxalate |
| 44 | 4-[(CH₃)₂N(CH₂)₂—O—]C₆H₄— | SO₂ | 1 | 2 | —CH(CH₃)₂ | carbonyl | —(CH₂)₂N(C₂H₅)₂ | 2 | —N(C₂H₅)₂ | oxalate |
| 45 | 4-CH₃SO₂—C₆H₄— | O | 1 | 2 | —CH(CH₃)₂ | carbonyl | —(CH₂)₃—N(CH₃)₂ | 3 | —N(CH₃)₂ | fumarate |
| 46 | 4-CH₃S—C₆H₄— | O | 1 | 2 | —CH(CH₃)₂ | carbonyl | —(CH₂)₃—N(C₂H₅)₂ | 3 | —N(C₂H₅)₂ | citrate |
| 47 | 4-CH₃S(O)—C₆H₄— | O | 1 | 2 | —CH(CH₃)₂ | carbonyl | —(CH₂)₃—N(C₃H₇)₂ | 3 | —N(C₃H₇)₂ | citrate |
| 48a | [4-(CH₃CONH—)—C₆H₄]— | O | 1 | 3 | —(CH₂)₂—N(C₂H₅)₂ | carbonyl | H | 2 | —N(C₂H₅)₂ | oxalate |
| 48b | [4-CH₃CO—CH₃O—C₆H₃]— | O | 1 | 3 | —(CH₂)₂—N(C₂H₅)₂ | cyano-iminomethyl | H | 2 | —N(C₂H₅)₂ | oxalate |
| 48c | 4-NH₂CO—C₆H₄— | O | 1 | 4 | —(CH₂)₂—N(C₂H₅)₂ | carbonyl | H | 2 | —N(C₂H₅)₂ | oxalate |
| 49 | C₆H₅— | SO₂ | 1 | 2 | —(CH₂)₂—N(C₂H₅)₂ | carbonyl | H | 2 | —N(C₂H₅)₂ | citrate hydrate [1:2:0.5] |
| 50a | C₆H₅— | O | 1 | 3 | [4-CH₃(C₆H₄)]— | carbonyl | —(CH₂)₃—C₄H₈N⁽ʰ⁾ | 3 | —C₄H₈N⁽ⁿ⁾ | maleate |
| 50b | C₆H₅— | O | 1 | 3 | [3-Br(C₆H₄)]— | carbonyl | —(CH₂)₃—C₄H₈N⁽ʰ⁾ | 3 | —C₄H₈N⁽ⁿ⁾ | maleate |
| 50c | C₆H₅— | O | 1 | 3 | 2,4,6-Br₃—C₆H₂— | carbonyl | —(CH₂)₃—C₄H₈N⁽ʰ⁾ | 3 | —C₄H₈N⁽ⁿ⁾ | maleate |
| 50d | C₆H₅— | O | 1 | 3 | [4-OCH₃(C₆H₄)]— | carbonyl | —(CH₂)₃—C₄H₈N⁽ʰ⁾ | 3 | —C₄H₈N⁽ⁿ⁾ | maleate |
| 50e | C₆H₅— | O | 1 | 3 | [4-NO₂(C₆H₄)]— | carbonyl | —(CH₂)₃—C₄H₈N⁽ʰ⁾ | 3 | —C₄H₈N⁽ⁿ⁾ | maleate |
| 50f | C₆H₅— | O | 1 | 3 | [3-CF₃(C₆H₄)]— | carbonyl | —(CH₂)₃—C₄H₈N⁽ʰ⁾ | 3 | —C₄H₈N⁽ⁿ⁾ | maleate |
| 50g | C₆H₅— | O | 1 | 3 | [4-CN(C₆H₄)]— | carbonyl | —(CH₂)₃—C₄H₈N⁽ʰ⁾ | 3 | —C₄H₈N⁽ⁿ⁾ | maleate |
| 51a | C₆H₅— | SO₂ | 1 | 2 | H | carbonyl | —(CH₂)₂N(CH₃)₂ | 2 | —N(CH₃)₂ | citrate |
| 51b | C₆H₅— | SO₂ | 1 | 2 | —CH(CH₃)₂ | carbonyl | —(CH₂)₂N(CH₃)₂ | 2 | —N(CH₃)₂ | citrate |
| 52 | C₆H₅— | SO₂ | 1 | 2 | —CH(CH₃)₂ | cyanoimino-methyl | —(CH₂)₂N(CH₃)₂ | 2 | —N(CH₃)₂ | citrate |

TABLE 1-continued

| Ex No. | Ar | x | d | n | Z | B | W | p | $-N\begin{smallmatrix}R^3\\R^4\end{smallmatrix}$ | Salt-Hydrate |
|---|---|---|---|---|---|---|---|---|---|---|
| 53a | $C_6H_5-$ | S(O) | 1 | 2 | $-(CH_2)_2N(C_2H_5)_2$ | cyanoimino-methyl | H | 2 | $-N(C_2H_5)_2$ | citrate |
| 53b | $C_6H_5-$ | — | 0 | 3 | $-(CH_2)_2N(C_2H_5)_2$ | cyanoimino-methyl | H | 2 | $-N(C_2H_5)_2$ | citrate |
| 53c | $C_6H_5-$ | S | 1 | 2 | $-(CH_2)_2N(C_2H_5)_2$ | cyanoimino-methyl | H | 2 | $-N(C_2H_5)_2$ | citrate |
| 53d | $C_6H_5-$ | O | 1 | 2 | $-(CH_2)_2N(C_2H_5)_2$ | cyanoimino-methyl | H | 2 | $-N(C_2H_5)_2$ | citrate |
| 54a | $4\text{-}CH_3\text{-}C_6H_4-$ | S | 1 | 2 | $-CH(CH_3)_2$ | cyanoimino-methyl | $-(CH_2)_2N(CH_3)_2$ | 2 | $-N(CH_3)_2$ | citrate |
| 54b | $(C_4H_3O)-CH_2-$ (f) | S(O) | 1 | 2 | $-CH(CH_3)_2$ | cyanoimino-methyl | $-(CH_2)_2N(CH_3)_2$ | 2 | $-N(CH_3)_2$ | citrate |
| 54c | 2-pyridinyl | — | 0 | 2 | H | cyanoimino-methyl | $-(CH_2)_2N(CH_3)_2$ | 2 | $-N(CH_3)_2$ | citrate |
| 54d | $4\text{-}NO_2\text{-}C_6H_4-$ | O | 1 | 2 | $-CH(CH_3)_2$ | cyanoimino-methyl | $-(CH_2)_2N(CH_3)_2$ | 2 | $-N(CH_3)_2$ | citrate |
| 55 | $C_6H_5-$ | $SO_2$ | 1 | 2 | $-(CH_2)_3N(C_2H_5)_2$ | thioxo-methyl | H | 2 | $-N(C_2H_5)_2$ | citrate |
| 56 | $C_6H_5-$ | O | 1 | 2 | $-(CH_2)_2N(C_2H_5)_2$ | thioxo-methyl | H | 2 | $-N(C_2H_5)_2$ | citrate |
| 57 | $C_6H_5-$ | S | 1 | 2 | $-(CH_2)_2N(C_2H_5)_2$ | thioxo-methyl | H | 2 | $-N(C_2H_5)_2$ | citrate |
| 58 | $C_6H_5-$ | — | 0 | 3 | $-(CH_2)_2N(C_2H_5)_2$ | thioxo-methyl | H | 2 | $-N(C_2H_5)_2$ | citrate |
| 59 | $C_6H_5-$ | S(O) | 1 | 2 | $-(CH_2)_2N(C_2H_5)_2$ | thioxo-methyl | H | 2 | $-N(C_2H_5)_2$ | citrate |
| 60 | $(C_4H_3O)-CH_2-$ (f) | S(O) | 1 | 2 | $-CH(CH_3)_2$ | thioxo-methyl | $-(CH_2)_3N(CH_3)_2$ | 3 | $-N(CH_3)_2$ | citrate |
| 61 | $3,5\text{-}Cl_2\text{-}C_6H_3-$ | $SO_2$ | 1 | 2 | $-CH(CH_3)_2$ | thioxo-methy | $-(CH_2)_2-C_4H_8NO$ (a) | 2 | $-C_4H_8NO$ (k) | citrate |
| 62 | 2-pyridinyl | — | 0 | 2 | H | carbonyl | $-(CH_2)_2-C_4H_8N$ (b) | 2 | $-C_4H_8N$ (n) | citrate |
| 63 | $C_6H_5-$ | $SO_2$ | 1 | 2 | $-CH(CH_3)_2$ | carbonyl | $-(CH_2)_2-N(C_2H_5)_2$ | 2 | $-N(C_2H_5)_2$ | — |
| 64 | $C_6H_5-$ | $SO_2$ | 1 | 2 | H | carbonyl | $-(CH_2)_2-N(C_2H_5)_2$ | 2 | $-N(C_2H_5)_2$ | — |

Footnotes:
(a)2-(4-morpholinyl)ethyl
(b)2-(1-pyrrolidinyl)ethyl
(c)2-(1-homopiperidinyl)ethyl
(d)2-(1-piperidinyl)ethyl
(e)1-piperidinyl
(f)(2-furanyl)methyl
(g)3-(4-morpholinyl)propyl
(h)3-(1-pyrrolidinyl)propyl
(i)2-(4-phenyl-1-piperazinyl)ethyl
(j)3-(4-phenyl-1-piperazinyl)propyl
(k)4-morpholinyl
(l)(4-phenyl)-1-piperazinyl
(m)4-methyl-1-piperazinyl
(n)1-pyrrolidinyl
(o)2-(4-methyl-1-piperazinyl)ethyl
(p)3-(4-methyl-1-piperazinyl)propyl

Pharmacology

The action of compounds of this invention in correcting cardiac arrhythmias or preventing cardiac arrhythmias is demonstrated by the following procedure:

Coronary Artery Ligation Induced Arrhythmias

Adult mongrel dogs which are in the conscious state were used for the test, and cardiac arrhythmias were induced by prior (22-24 hr) surgical preparation in which blood flow through a coronary artery was occluded by use of a constrictor device as reported by Smith et al.[1] A Grass Model 79 polygraphy was used for recording the electrocardiogram (Grass 7P4 preamplifier).

[1] Cardiac arrhythmias produced by modification of method of Harris, 1950, Circulation 1, 1318, as reported by Smith et al, 1973, Pharmacologist 15, 192.

The test compound was administered by infusion (Harvard Model 942 Infusion Pump) into a saphenous vein to one group of dogs at a rate of 0.5 mg/kg/min. Concentration of the test compound was adjusted according to the weight of the dog to allow a volume of infusion of 0.5 ml/min. The test compound was administered orally by gavage to another group of dogs to allow a volume of infusion of 0.5 ml/min. The test compound was administered orally by gavage to another group of dogs at dose levels of 10 through 20 mg/kg. The test compound was prepared in distilled water to give a total volume of 20 ml. Following the administration of the test compound, the heart rate, number of ectopic cardiac beats per min, and the percent ectopic beats (ectopic beats/HR X100) were recorded at 15 min intervals. The compound was considered active if it abolished the ectopic ventricular frequency and caused a return to normal sinus rhythm within 2 hours of administration. The preferred compounds of the present invention, the arylsulfonylureas, were shown to be effective when administered at a correcting dose range of about 1 to 18 mg/kg intravenously.

Pharmaceutical Compositions

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting carriers or excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil; e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablet, capsules, ampoules and suppositories are examples of preferred dosage forms according to the invention. It is only necessary that the active ingredient constitute an effective amount, i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests that the oral dosage effective to correct arrhythmias will be about 3 times that of the intravenous dosage. The animal data also suggest dosage requirements will be about half that of quinidine for the more active compounds.

Based on the animal data, allowing for variation in species and severity of cardiac arrhythmia unit dosages containing an amount of compound equivalent to about 1 to about 100 mg/kg of body weight, are contemplated. Based on all of the above considerations, a choice in a range of unit oral dosages for humans of about 10 to about 1000 mg is contemplated, preferably about 10 to 600 mg. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Capsules | |
|---|---|
| Ingredients | Per Cap. |
| 1. Active ingredient | 10.0 mg |
| 2. Lactose | 146.0 mg |
| 3. Magnesium Stearate | 4.0 mg |
| | 160.0 mg |

Procedure

Step 1. Blend ingredients 1, 2 and 3.

Step 2. Pass blend from Step 1 through a No. 30 mesh screen (0.59 mm) and blend again.

Step 3. Fill powder blend from Step 2 into No. 1 hard gelatin capsules.

| Ingredients | Mg./Tab. |
|---|---|
| Tablets (10 mg) | |
| 1. Active ingredient | 10.0 mg |
| 2. Corn starch | 20.0 mg |
| 3. Alginic acid | 20.0 mg |
| 4. Sodium alginate | 20.0 mg |
| 5. Magnesium stearate | 1.3 mg |
| | 71.3 mg |
| Tablets (50 mg) | |
| 1. Active ingredient | 50.0 mg |
| 2. Milo starch | 20.0 mg |
| 3. Corn starch | 38.0 mg |
| 4. Lactose | 90.0 mg |
| 5. Magnesium stearate | 2.0 mg |
| | 200.0 mg |

Procedure

Step 1. Blend ingredients 1, 2 and 3 and 4.

Step 2. Add sufficient water portionwise to the blend from Step 1 with careful stirring after each addition. Such additions of water and stirring continue until the mass is of a consistency to permit is conversion to wet granules.

Step 3. The wet mass prepared in Step 2 is converted to granules by passing it through an oscillating granulator, using a #8-mesh (2.36 mm) screen.

Step 4. The wet granules prepared in Step 3 are dried in an oven at 140° F.

Step 5. Dried granules from Step 4 are passed through an oscillating granulator, using a No. 10-mesh (2.00 mm) screen.

Step 6. Lubricate the dry granules from Step 5 by blending with ingredient No. 5.

Step 7. The lubricated granules from Step 6 are compressed on a suitable tablet press.

| Intravenous Injection | |
|---|---|
| Ingredients | Per ml. |
| 1. Active ingredient | 1.0 mg |
| 2. Isotonic pH 4.0 buffer solution | q.s. to 1.0 ml |

Procedure

Step 1. Dissolve the active ingredient in the buffer solution.

Step 2. Aseptically filter the solution from Step 1.

Step 3. The sterile solution is now aseptically filled into sterile ampuls.

Step 4. The ampuls are sealed under aseptic conditions.

| Intramuscular Injection | |
|---|---|
| Ingredients | Per ml. |
| 1. Acitive ingredients | 5.0 mg |
| 2. Isotonic pH 4.0 buffer solution | q.s. to 1.0 ml |

Procedure

Step 1. Dissolve the active ingredient in the buffer solution.

Step 2. Aseptically filter the solution from Step 1.

Step 3. The sterile solution is now aseptically filled into sterile ampuls.

Step 4. The ampuls are sealed under aseptic conditions.

| Suppositories | |
|---|---|
| Ingredients | Per Supp. |
| 1. Active ingredient | 10.0 mg |
| 2. Polyethylene Glycol 1000 | 1350.0 mg |
| 3. Polyethylene Gylcol 4000 | 450.0 mg |
| | 1810.0 mg |

Procedure

Step 1. Melt ingredients 2 and 3 together and stir until uniform.

Step 2. Dissolve 1 in the molten mass from Step 1 and stir until uniform.

Step 3. Pour the molten mass from Step 2 into suppository molds and allow to cool.

Step 4. Remove the suppositories from molds and wrap.

Therapeutic compositions having cardiac arrhythmia inhibiting activity in dosage unit form, comprising a pharmaceutical carrier and a cardiac arrhythmia inhibiting amount of a compound of Formula I or pharmaceutically acceptable salts thereof are therefore an embodiment of this invention.

Varius modifications and equivalents will be apparent to one skilled in the art and may be made in the compounds, method, and compositions of the present invention without departing from the spirit or scope thereof, and it is therefore to be understood that the invention is to be limited only by the scope of the appended claims.

What is claimed is:

1. A compound comprising the structure:

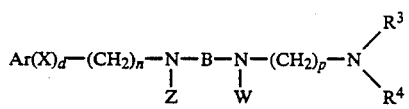

wherein;

Ar is 1- and 2-naphthyl, 2,3-dihydro-1H-inden-4(or5)-yl, 2-furanylmethyl, 2-pyridinyl, phenyl and phenyl substituted by one to three radicals, the same or different, selected from the group consisting of loweralkyl, loweralkoxy, diloweralkylamino, cyano, loweralkylthio, loweralkylsulfinyl, loweralkylsulfonyl, acyl, acylamino, aminocarbonyl, diloweralkylaminoloweralkoxy, trifluoromethyl, nitro and halogen;

X is thio, sulfinyl, sulfonyl, or oxygen;

d is zero or one;

B is carbonyl, thioxomethyl;

n, m and p are selected from 2–6 inclusive and may be the same or different;

Z and W are each R or

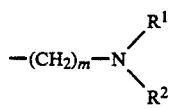

with the proviso that when Z is R, W is $-(CH_2)_m-NR^1R^2$ and when Z is $-(CH_2)_m-NR^1R^2$, W is R;

R, $R^1$, $R^2$, $R^3$ and $R^4$ may be the same or different and are selected from the group consisting of hydrogen, loweralkyl, cycloalkyl, phenyl and phenylloweralkyl wherein phenyl may be substituted by one to three radicals, the same or different, said radicals being selected from the group consisting of loweralkyl, loweralkoxy, cyano, trifluoromethyl, nitro and halogen, and each of $R^1$ and $R^2$, and $R^3$ and $R^4$ may, together with the adjacent nitrogen form the heterocyclic ring structure 1-homopiperidinyl, 1-piperidinyl, 4-morpholinyl, 1-pyrrolidinyl, 1-piperazinyl, or piperazine substituted in the 4-position by a radical selected from loweralkyl, phenyl, phenyl substituted by 1–2 radicals selected from halo, loweralkyl, loweralkoxy, trifluoromethyl, nitro, and cyano and pyridyl;

with the further proviso that when B is thioxomethyl, then $R^1$, $R^2$, $R^3$ and $R^4$ are not hydrogen or with the adjacent nitrogen from the heterocyclic ring structure 1-piperazinyl; and with a still further proviso that when B is carbonyl and $(X)_d$ is thio or sulfinyl or Ar is phenyl substituted by loweralkyltho or loweralkylsulfinyl, then $R^1$, $R^2$, $R^3$ and $R^4$ are not hydrogen or with the adjacent nitrogen form the heterocyclic ring structure 1-piperazinyl;

and the pharmaceutically acceptable salts thereof.

2. The compound of claim 1 wherein said compound is N'-[2-(diethylamino)ethyl]-N-[3-(diethylamino)- propyl]-N-[2-(phenylsulfonyl)ethyl]urea or a pharmaceutically acceptable salt thereof.

3. The compound of claim 1 wherein said compound is N,N'-bis[2-(diethylamino)ethyl]-N-[2-(phenylsulfonyl)ethyl]urea or a pharmaceutically acceptable salt thereof.

4. The compound of claim 1 wherein said compound is N'-[2-(diethylamino)ethyl]-N-[2-(4-morpholinyl)ethyl]-N-[2-(phenylthio)ethyl]urea or a pharmaceutically acceptable salt thereof.

5. The compound of claim 1 wherein said compound is N'-[2-(diethylamino)ethyl]-N-[2-(phenylsulfonyl)ethyl]-N-[2-(1-pyrrolidinyl)ethyl]urea or a pharmaceutically acceptable salt thereof.

6. The compound of claim 1 wherein said compound is N-[2-(diethylamino)ethyl]-N'-[2-(methylphenylamino)ethyl]-N-[2-(phenylsulfonyl)ethyl]urea or a pharmaceutically acceptable salt thereof.

7. The compound of claim 1 wherein said compound is N'-[2-(diethylamino)ethyl]-N-[2-(homopiperidinyl)ethyl]-N-[2-(phenylsulfonyl)ethyl]urea or a pharmaceutically acceptable salt thereof.

8. The compound of claim 1 wherein said compound is N-[2-(diethylamino)ethyl]-N'-[3-(diethylamino)propyl]-N-[2-(phenylsulfonyl)ethyl]urea or a pharmaceutically acceptable salt thereof.

9. The compound of claim 1 wherein said compound is N'-[2-(diethylamino)ethyl]-N-[2-(methylphenylamino)ethyl]-N-[2-(phenylsulfonyl)ethyl]urea or a pharmaceutically acceptable salt thereof.

10. The compound of claim 1 wherein said compound is N'-[2-(diethylamino)ethyl]-N-[2-(phenylsulfonyl)ethyl]-N-[2-(1-piperidinyl)ethyl]urea or a pharmaceutically acceptable salt thereof.

11. The compound of claim 1 wherein said compound is N'-[2-(diethylamino)ethyl]-N-[2-(dimethylamino)ethyl]-N-[2-(phenylsulfonyl)ethyl]urea or a pharmaceutically acceptable salt thereof.

12. The compound of claim 1 wherein said compound is N-[2-(diethylamino)ethyl]-N-[2-(phenylsulfonyl)ethyl]-N'-[2-(1-piperidinyl)ethyl]urea or a pharmaceutically acceptable salt thereof.

13. The compound of claim 1 wherein said compound is N-[2-(diethylamino)ethyl]-N'-[3-(diethylamino)propyl]-N-[2-(phenylsulfonyl)ethyl]thiourea or a pharmaceutically acceptable salt thereof.

14. The compound of claim 1 wherein said compound is N,N'-bis[2-(dimethylamino)ethyl]-N-(2-phenoxyethyl)urea or a pharmaceutically acceptable salt thereof.

15. The compound of claim 1 wherein said compound is N,N'-bis[2-(diethylamino)ethyl]-N-[2-(phenylthio)ethyl]urea or a pharmaceutically acceptable salt thereof.

16. The compound of claim 1 wherein said compound is N,N'-bis[2-(diethylamino)ethyl]-N-(3-phenylpropyl)urea or a pharmaceutically acceptable salt thereof.

17. The compound of claim 1 wherein said compound is N,N'-bis[2-(diethylamino)ethyl]-N-[2-(phenylsulfinyl)ethyl]urea or a pharmaceutically acceptable salt thereof.

18. The compound of claim 1 wherein said compound is N,N'-bis[3-(diethylamino)propyl]-N-[2-(phenylsulfonyl)ethyl]urea or a pharmaceutically acceptable salt thereof.

19. The compound of claim 1 wherein said compound is N-[4-(diethylamino)butyl]-N'-[2-(diethylamino)ethyl]-N-[2-(phenylsulfonyl)ethyl]urea or a pharmaceutically acceptable salt thereof.

20. The compound of claim 1 wherein said compound is N,N-bis[2-(diethylamino)ethyl]-N'-(1-methylethyl)-N'-[2-(phenylsulfonyl)ethyl]urea or a pharmaceutically acceptable salt thereof.

21. The compound of claim 1 wherein said compound is N,N-bis[2-(diethylamino)ethyl]-N'-[2-(phenylsulfonyl)ethyl]urea or a pharmaceutically acceptable salt thereof.

22. A method for treating cardiac arrhythmia in a living mammal, the method comprising administering to the mammal an effective amount of a compound having the structure:

$$Ar(X)_d-(CH_2)_n-\underset{Z}{N}-B-\underset{W}{N}-(CH_2)_p-N\begin{matrix}R^3\\ \\R^4\end{matrix}$$

wherein;
Ar is 1- and 2-naphthyl, 2,3-dihydro-1H-inden-4(or 5)-yl, 2-furanylmethyl, 2-pyridinyl, phenyl and phenyl substituted by one to three radicals, the same or different, said radicals being selected from the group consisting of loweralkyl, loweralkoxy, diloweralkylamino, cyano, loweralkylthio, loweralkylsulfinyl, loweralkylsulfonyl, acyl, acylamino, aminocarbonyl, diloweralkylaminoloweralkoxy, trifluoromethyl, nitro and halogen;
X is thio, sulfinyl, sulfonyl, or oxygen;
d is zero or one;
B is carbonyl, thioxomethyl;
n, m and p are selected from 2–6 inclusive and may be the same or different;
Z and W are each R or $$-(CH_2)_m-N\begin{matrix}R^1\\ \\R^2\end{matrix},$$

with the proviso that when Z is R, W is $-(CH_2)_m-NR^1R^2$ and when Z is $-(CH_2)_m-NR^1R^2$, W is R;
R, $R^1$, $R^2$, $R^3$ and $R^4$ may be the same or different are are selected from the group consisting of hydrogen, loweralkyl, cycloalkyl, phenyl and phenylloweralkyl wherein phenyl may be substituted by one to three radicals, the same or different, selected from the group consisting of loweralkyl, loweralkoxy, cyano, trifluoromethyl, nitro and halogen;
each of $R^1$ and $R^2$, and $R^3$ and $R^4$ may, together with the adjacent nitrogen form the heterocyclic ring structure 1-bomopiperidinyl, 1-piperidinyl, 4-morpholinyl, 1-pyrrolidinyl, 1-piperazinyl, or piperazine substituted in the 4-position by a radical selected from loweralkyl, phenyl, phenyl substituted by 1–2 radicals selected from halo, loweralkyl, loweralkoxy, trifluoromethyl, nitro and cyano and pyridyl;
with the further proviso that when B is thioxomethyl, then $R^1$, $R^2$, $R^3$ and $R^4$ are not hydrogen or with the adjacent nitrogen from the heterocyclic ring structure 1-piperazinyl; and
with a still further proviso that when B is carbonyl and $(X)_d$ is thio or sulfinyl or Ar is phenyl substituted by loweralkylthio or loweralkylsulfinyl, then $R^1$, $R^2$, $R^3$ and $R^4$ are not hydrogen or with the adjacent nitrogen form the heterocyclic ring structure 1-piperazinyl;
and the pharmaceutically acceptable salts thereof.

23. The method of claim 22 wherein the compound administered is N'-[2-(diethylamino)ethyl]-N-[3-(diethylamino)propyl]-N-[2-(phenylsulfonyl)ethyl]urea or a pharmaceutically acceptable salt thereof.

24. The method of claim 22 wherein the compound administered is N,N'-bis[2-(diethylamino)ethyl]-N-[2-(phenylsulfonyl)ethyl]urea or a pharmaceutically acceptable salt thereof.

25. The method of claim 22 wherein the compound administered is N'-[2-(diethylamino)ethyl]-N-[2-(4-morpholinyl)ethyl]-N-[2-(phenylthio)ethyl]urea or a pharmaceutically acceptable salt thereof.

26. The method of claim 22 wherein the compound administered is N'-[2-(diethylamino)ethyl]-N-[2-(phenylsulfonyl)ethyl]-N-[2-(1-pyrrolidinyl)ethyl]urea or a pharmaceutically acceptable salt thereof.

27. The method of claim 22 wherein the compound administered is N-[2-(diethylamino)ethyl]-N'-[2-(methylphenylamino)ethyl]-N-[2-(phenylsulfonyl)ethyl]urea or a pharmaceutically acceptable salt thereof.

28. The method of claim 22 wherein the compound administered is N'-[2-(diethylamino)ethyl]-N-[2-(homopiperidinyl)ethyl]-N-[2-(phenylsulfonyl)ethyl]urea or a pharmaceutically acceptable salt thereof.

29. The method of claim 22 wherein the compound administered is N-[2-(diethylamino)ethyl]-N'-[3-(diethylamino)propyl]-N-[2-(phenylsulfonyl)ethyl]urea or a pharmaceutically acceptable salt thereof.

30. The method of claim 22 wherein the compound administered is N'-[2-(diethylamino)ethyl]-N-[2-(methylphenylamino)ethyl]-N-[2-(phenylsulfonyl)ethyl]urea or a pharmaceutically acceptable salt thereof.

31. The method of claim 22 wherein the compound administered is N'-[2-(diethylamino)ethyl]-N-[2-(phenylsulfonyl)ethyl]-N-[2-(1-piperidinyl)ethyl]urea or a pharmaceutically acceptable salt thereof.

32. The method of claim 22 wherein the compound administered is N'-[2-(diethylamino)ethyl]-N-[2-(dimethylamino)ethyl]-N-[2-(phenylsulfonyl)ethyl]urea or a pharmaceutically acceptable salt thereof.

33. The method of claim 22 wherein the compound administered is N-[2-(diethylamino)ethyl]-N-[2-(phenylsulfonyl)ethyl]-N'-[2-(1-piperidinyl)ethyl]urea or a pharmaceutically acceptable salt thereof.

34. The method of claim 22 wherein the compound administered is N-[2-(diethylamino)ethyl]-N'-[3-(diethylamino)propyl]-N-[2-(phenylsulfonyl)ethyl]thiourea or a pharmaceutically acceptable salt thereof.

35. The method of claim 22 wherein the compound administered is N,N'-bis[2-(dimethylamino)ethyl]-N-(2-phenoxyethyl)urea or a pharmaceutically acceptable salt thereof.

36. The method of claim 22 wherein the compound administered is N,N'-bis[2-(diethylamino)ethyl]-N-[2-(phenylthio)ethyl]urea or a pharmaceutically acceptable salt thereof.

37. The method of claim 22 wherein the compound administered is N,N'-bis[2-(diethylamino)ethyl]-N-(3-phenylpropyl)urea or a pharmaceutically acceptable salt thereof.

38. The method of claim 22 wherein the compound administered is N,N'-bis[2-(diethylamino)ethyl]-N-[2-(phenylsulfinyl)ethyl]urea or a pharmaceutically acceptable salt thereof.

39. The method of claim 22 wherein the compound administered is N,N'-bis[3-(diethylamino)propyl]-N-[2-(phenylsulfonyl)ethyl]urea or a pharmaceutically acceptable salt thereof.

40. The method of claim 22 wherein the compound administered is N-[4-(diethylamino)butyl]-N'-[2-(diethylamino)ethyl]-N-[2-(phenylsulfonyl)ethyl]urea or a pharmaceutically acceptable salt thereof.

41. The method of claim 22 wherein the compound administered is N,N-bis[2-(diethylamino)ethyl]-N'-(1-methylethyl)-N'-[2-(phenylsulfonyl)ethyl]urea or a pharmaceutically acceptable salt thereof.

42. The method of claim 22 wherein the compound administered is N,N-bis[2-(diethylamino)ethyl]-N'-[2-(phenylsulfonyl)ethyl]urea or a pharmaceutically acceptable salt thereof.

43. A pharmaceutical composition for the treatment of cardiac arrhythmia comprising:

(a) a compound having the structure:

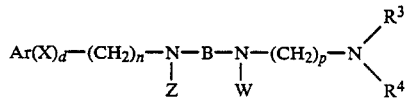

Ar is 1- and 2-naphthyl, 2,3-dihydro-1H-inden-4(or 5)-yl, 2-furanylmethyl, 2-pyridinyl, phenyl and phenyl substituted by one to three radicals, the same or different, said radicals being selected from the group consisting of loweralkyl, loweralkoxy, diloweralkylamino, cyano, loweralkylthio, loweralkylsulfinyl, loweralkylsulfonyl, acyl, acylamino, aminocarbonyl, diloweralkylaminoloweralkoxy, trifluoromethyl, nitro and halogen;

X is thio, sulfinyl, sulfonyl, or oxygen;

d is zero or one;

B is carbonyl, thioxomethyl;

n, m and p are selected from 2–6 inclusive and may be the same or different;

Z and W are each R or

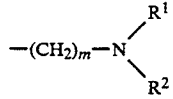

with the proviso that when Z is R, W is $-(CH_2)_m-NR^1R^2$ and when Z is $-(CH_2)_m-NR^1,R^2$, W is R;

R, $R^1$, $R^2$, $R^3$ and $R^4$ may be the same or different are selected from the group consisting of hydrogen, loweralkyl, cycloalkyl, phenyl and phenylloweralkyl wherein phenyl may be substituted by one to three radicals, the same or different, said radicals being selected from the group consisting of loweralkyl, loweralkoxy, cyano, trifluoromethyl, nitro and halogen;

each of $R^1$ and $R^2$, and $R^3$ and $R^4$ may together with the adjacent nitrogen form the heterocyclic ring structure 1-homopiperidinyl, 1-piperidinyl, 4-morpholinyl, 1-pyrrolidinyl, 1-piperazinyl, or piperazine substituted in the 4-position by a radical selected from loweralkyl, phenyl, phenyl substituted by 1–2 radicals selected from halo, loweralkyl, loweralkoxy, trifluoromethyl, nitro and cyano and pyridyl; with the further proviso that when B is thioxomethyl, then $R^1$, $R^2$, $R^3$ and $R^4$ are not hydrogen or with the adjacent nitrogen form the heterocyclic ring structure 1-piperazinyl; and with a still further proviso that when B is carbonyl and $(X)_d$ is thio or sulfinyl or Ar is phenyl substituted by loweralkylthio or loweralkylsulfinyl, then $R^1$, $R^2$, $R^3$ and $R^4$ are not hydrogen or with the adjacent nitrogen form the heterocyclic ring structure 1-piperazinyl;

and the pharmaceutically acceptable salts thereof;

(b) a pharmaceutical carrier therefor.

44. The pharmaceutical composition of claim 43 wherein said compound is N'-[2-(diethylamino)ethyl]-N-[3-(diethylamino)propyl]-N-[2-(phenylsulfonyl)ethyl]urea or a pharamaceutically acceptable salt thereof.

45. The pharmaceutical composition of claim 43 wherein said compound is N,N'-bis[2-(diethylamino)ethyl]-N-[2-(phenylsulfonyl)ethyl]urea or a pharmaceutically acceptable salt thereof.

46. The pharmaceutical composition of claim 43 wherein said compound is N'-[2-(diethylamino)ethyl]-N-[2-(4-morpholinyl)ethyl]-N-[2-(phenylthio)ethyl]urea or a pharmaceutically acceptable salt thereof.

47. The pharmaceutical composition of claim 43 wherein said compound is N'-[2-(diethylamino)ethyl]-N-[2-(phenylsulfonyl)ethyl]-N-[2-(1-pyrrolidinyl)ethyl]urea or a pharmaceutically acceptable salt thereof.

48. The pharmaceutical composition of claim 43 wherein said compound is N-[2-(diethylamino)ethyl]-N'-[2-(methylphenylamino)ethyl]-N-[2-(phenylsulfonyl)ethyl]urea or a pharmaceutically acceptable salt thereof.

49. The pharmaceutical composition of claim 43 wherein said compound is N'-[2-(diethylamino)ethyl]-N-[2-(homopiperidinyl)ethyl]-N-[2-(phenylsulfonyl)ethyl]urea or a pharmaceutically acceptable salt thereof.

50. The pharmaceutical composition of claim 43 wherein said compound is N-[2-(diethylamino)ethyl]-N'-[3-(diethylamino)propyl]-N-[2-(phenylsulfonyl)ethyl]urea or a pharmaceutically acceptable salt thereof.

51. The pharmaceutical composition of claim 43 wherein said compound is N'-[2-(diethylamino)ethyl]-N-[2-(methylphenylamino)ethyl]-N-[2-(phenylsulfonyl)ethyl]urea or a pharmaceutically acceptable salt thereof.

52. The pharmaceutical composition of claim 43 wherein said compound is N'-[2-(diethylamino)ethyl]-N-[2-(phenylsulfonyl)ethyl]-N-[2-(1-piperidinyl)ethyl]urea or a pharmaceutically acceptable salt thereof.

53. The pharmaceutical composition of claim 43 wherein said compound is N'-[2-(diethylamino)ethyl]-N-[2-(dimethylamino)ethyl]-N-[2-(phenylsulfonyl)ethyl]urea or a pharmaceutically acceptable salt thereof.

54. The pharmaceutical composition of claim 43 wherein said compound is N-[2-(diethylamino)ethyl]-N-[2-(phenylsulfonyl)ethyl]-N'-[2-(1-piperidinyl)ethyl]urea or a pharmaceutically acceptable salt thereof.

55. The pharmaceutical composition of claim 43 wherein said compound is N-[2-(diethylamino)ethyl]-N'-[3-(diethylamino)propyl]-N-[2-(phenylsulfonyl)ethyl]thiourea or a pharmaceutically acceptable salt thereof.

56. The pharmaceutical composition of claim 43 wherein said compound is N,N'-bis[2-(dimethylamino)ethyl]-N-(2-phenoxyethyl)urea or a pharmaceutically acceptable salt thereof.

57. The pharmaceutical composition of claim 43 wherein said compound is N,N'-bis[2-(diethylamino)ethyl]-N-[2-(phenylthio)ethyl]urea or a pharmaceutically acceptable salt thereof.

58. The pharmaceutical composition of claim 43 wherein said compound is N,N'-bis[2-(diethylamino)ethyl]-N-(3-phenylpropyl)urea or a pharmaceutically acceptable salt thereof.

59. The pharmaceutical composition of claim 43 wherein said compound is N,N'-bis[2-(diethylamino)ethyl]-N-[2-(phenylsulfinyl)ethyl]urea or a pharmaceutically acceptable salt thereof.

60. The pharmaceutical composition of claim 43 wherein said compound is N,N'-bis[3-(diethylamino)propyl]-N-[2-(phenylsulfonyl)ethyl]urea or a pharmaceutically acceptable salt thereof.

61. The pharmaceutical composition of claim 43 wherein said compound is N-[4-(diethylamino)butyl]-N'-[2-(diethylamino)ethyl]-N-[2-(phenylsulfonyl)ethyl]urea or a pharmaceutically acceptable salt thereof.

62. The pharmaceutical composition of claim 43 wherein said compound is N,N-bis[2-(diethylamino)ethyl]-N'-(1-methylethyl)-N'-[2-(phenylsulfonyl)ethyl]urea or a pharmaceutically acceptable salt thereof.

63. The pharmaceutical composition of claim 43 wherein said compound is N,N-bis[2-(diethylamino)ethyl]-N'-[2-(phenylsulfonyl)ethyl]urea or a pharmaceutically acceptable salt thereof.

* * * * *